(12) United States Patent
Martin et al.

(10) Patent No.: US 8,603,820 B2
(45) Date of Patent: *Dec. 10, 2013

(54) DERIVATIZED PEPTIDE-CONJUGATED (METH) ACRYLATE CELL CULTURE SURFACE AND METHODS OF MAKING

(75) Inventors: Arthur W. Martin, Horseheads, NY (US); Shawn M. O'Malley, Horseheads, NY (US); Simon K. Shannon, Horseheads, NY (US); Christopher B. Shogbon, Corning, NY (US); Carl M. Truesdale, Corning, NY (US); Yue Zhou, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 495 days.

This patent is subject to a terminal disclaimer.

(21) Appl. No.: 12/783,125

(22) Filed: May 19, 2010

(65) Prior Publication Data

US 2011/0275154 A1    Nov. 10, 2011

Related U.S. Application Data

(60) Provisional application No. 61/180,279, filed on May 21, 2009.

(51) Int. Cl.
*C12N 5/07* (2010.01)

(52) U.S. Cl.
USPC .......................................................... 435/402

(58) Field of Classification Search
None
See application file for complete search history.

(56) References Cited

U.S. PATENT DOCUMENTS

| 4,766,160 A * | 8/1988 | Bichon et al. ................... 522/46 |
| 2009/0191627 A1 * | 7/2009 | Fadeev et al. ................. 435/366 |

* cited by examiner

*Primary Examiner* — Jon P Weber
*Assistant Examiner* — Robert Yamasaki
(74) *Attorney, Agent, or Firm* — Susan S Wilks

(57) ABSTRACT

A synthetic cell culture surface, prepared from a mixture of at least three (meth)acrylate monomers where one of the monomers has an N-hydroxysuccinimide moiety is provided, which supports the growth of cells including undifferentiated human embryonic stem cells in defined media. Methods for preparing the cell culture surface is also provided.

16 Claims, 8 Drawing Sheets

SEQUENCE LISTING

```
<160> NUMBER OF SEQ ID NOS: 23

<210> SEQ ID NO 1
<211> LENGTH: 15
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 1

Lys Gly Gly Asn Gly Glu Pro Arg Gly Asp Thr Tyr Arg Ala Tyr
1               5                   10                  15

<210> SEQ ID NO 2
<211> LENGTH: 12
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 2

Asn Gly Glu Pro Arg Gly Asp Thr Tyr Arg Ala Tyr
1               5                   10

<210> SEQ ID NO 3
<211> LENGTH: 7
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 3

Gly Arg Gly Asp Ser Pro Lys
1               5

<210> SEQ ID NO 4
<211> LENGTH: 12
<212> TYPE: PRT
<213> ORGANISM: ARTIFICIAL SEQUENCE
```

```
<220> FEATURE:
<223> OTHER INFORMATION: SYNTHETIC PEPTIDE

<400> SEQUENCE: 4

Ala Val Thr Gly Arg Gly Asp Ser Pro Ala Ser Ser
1               5                   10

<210> SEQ ID NO 5
<211> LENGTH: 12
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 5

Pro Gln Val Thr Arg Gly Asp Val Phe Thr Met Pro
1               5                   10

<210> SEQ ID NO 6
<211> LENGTH: 10
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 6

Arg Asn Ile Ala Glu Ile Ile Lys Asp Ile
1               5                   10

<210> SEQ ID NO 7
<211> LENGTH: 15
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 7

Lys Tyr Gly Arg Lys Arg Leu Gln Val Gln Leu Ser Ile Arg Thr
1               5                   10                  15

<210> SEQ ID NO 8
<211> LENGTH: 11
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 8

Asn Gly Glu Pro Arg Gly Asp Thr Arg Ala Tyr
1               5                   10

<210> SEQ ID NO 9
<211> LENGTH: 12
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 9

Asn Gly Glu Pro Arg Gly Asp Thr Tyr Arg Ala Tyr
1               5                   10

<210> SEQ ID NO 10
<211> LENGTH: 15
<212> TYPE: PRT
<213> ORGANISM: ARTIFICIAL SEQUENCE
<220> FEATURE:
<223> OTHER INFORMATION: SYNTHETIC PEPTIDE
```

```
<400> SEQUENCE: 10

Lys Tyr Gly Ala Ala Ser Ile Lys Val Ala Val Ser Ala Asp Arg
1               5                   10                  15

<210> SEQ ID NO 11
<211> LENGTH: 15
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 11

Lys Tyr Gly Lys Ala Phe Asp Ile Thr Tyr Val Arg Leu Lys Phe
1               5                   10                  15

<210> SEQ ID NO 12
<211> LENGTH: 16
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 12

Lys Tyr Gly Ser Glu Thr Thr Val Lys Tyr Ile Phe Arg Leu His Glu
1               5                   10                  15

<210> SEQ ID NO 13
<211> LENGTH: 16
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 13

Lys Tyr Gly Thr Asp Ile Arg Val Thr Leu Asn Arg Leu Asn Thr Phe
1               5                   10                  15

<210> SEQ ID NO 14
<211> LENGTH: 12
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 14

Thr Ser Ile Lys Ile Arg Gly Thr Tyr Ser Glu Arg
1               5                   10

<210> SEQ ID NO 15
<211> LENGTH: 12
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 15

Thr Trp Tyr Lys Ile Ala Phe Gln Arg Asn Arg Lys
1               5                   10

<210> SEQ ID NO 16
<211> LENGTH: 20
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 16
```

```
Ser Ile Asn Asn Asn Arg Trp His Ser Ile Tyr Ile Thr Arg Phe Gly
1               5                  10                  15

Asn Met Gly Ser
            20

<210> SEQ ID NO 17
<211> LENGTH: 13
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 17

Lys Tyr Gly Leu Ala Leu Glu Arg Lys Asp His Ser Gly
1               5                  10

<210> SEQ ID NO 18
<211> LENGTH: 17
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 18

Gly Gln Lys Cys Ile Val Gln Thr Thr Ser Trp Ser Gln Cys Ser Lys
1               5                  10                  15

Ser

<210> SEQ ID NO 19
<211> LENGTH: 17
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 19

Lys Gly Gly Lys Asp Gly Glu Pro Arg Gly Asp Thr Tyr Arg Ala Thr
1               5                  10                  15

Asp

<210> SEQ ID NO 20
<211> LENGTH: 13
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 20

Lys Gly Gly Leu Glu Pro Arg Gly Asp Thr Tyr Arg Asp
1               5                  10

<210> SEQ ID NO 21
<211> LENGTH: 17
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 21

Lys Gly Gly Cys Asn Gly Glu Pro Arg Gly Asp Thr Tyr Arg Ala Thr
1               5                  10                  15

Cys

<210> SEQ ID NO 22
```

```
<211> LENGTH: 13
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 22

Lys Gly Gly Cys Glu Pro Arg Gly Asp Thr Tyr Arg Cys
1               5                   10

<210> SEQ ID NO 23
<211> LENGTH: 15
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 23

Lys Gly Gly Ala Val Thr Gly Asp Gly Asn Ser Pro Ala Ser Ser
1               5                   10                  15
```

DERIVATIZED PEPTIDE-CONJUGATED (METH) ACRYLATE CELL CULTURE SURFACE AND METHODS OF MAKING

CLAIMING BENEFIT OF PRIOR FILED U.S. APPLICATION

This application claims the benefit of U.S. Provisional Application Ser. No. 61/180,279, filed on May 21, 2009. The content of this document and the entire disclosure of publications, patents, and patent documents mentioned herein are incorporated by reference.

FIELD

The present invention relates generally to surfaces and surface treatments to support cell culture, and methods of making the surfaces. More specifically, the present invention relates to N-hydroxysuccinimide derivatized (meth)acrylate monomers used, in combination with other (meth)acrylate compounds and combinations of (meth)acrylate compounds as cell culture surfaces. The present invention also provides methods of making and methods of using the cell culture surfaces.

SEQUENCE LISTING

This application contains a Sequence Listing electronically submitted via EFS-Web to the United States Patent and Trademark Office as text filed named "SEQUENCE_LISTING_SP09-149_ST25.txt" having a size of 6 kb and created on Jul. 21, 2011. Due to the electronic filing of the Sequence Listing, the electronically submitted Sequence Listing serves as both the paper copy required by 37 CFR §1.821(c) and the CRF required by §1.821(e). The information contained in the Sequence Listing is hereby incorporated herein by reference.

BACKGROUND

In vitro culturing of cells has been a useful research tool, providing material necessary for research in pharmacology, physiology and toxicology. Recent advances in the field of developmental biology, significantly in the isolation, growth and differentiation of stem cells, have opened the door for cell culture to provide material for therapeutic applications as well. Embryonic stem cells, including human embryonic stem cells, may be able to provide answers to difficult medical problems such as Alzheimer's disease, Parkinson's disease, diabetes, spinal cord injury, heart disease, and other debilitating and often fatal conditions.

Embryonic stem cells represent an example of difficult-to-culture cell types. Embryonic stem cells are particularly difficult to culture, difficult to control, and often require a specialized cell culture surface that can facilitate growth and proliferation of these cells in their undifferentiated state. Many coatings and surface enhancements have been developed to provide cell culture surfaces which promote cell growth in vitro. Some of these coatings and surface enhancements provide surfaces that support the culture of difficult-to-culture cells such as embryonic stem cells. However, many of these surfaces contain animal-derived additives such as proteins or cell extracts. These additives introduce a risk of infection into the preparation of therapeutic cells. For example, the use of extra-cellular matrix proteins derived from animals may introduce infective agents such as viruses or prions. These infective agents may be taken up by cells in culture and, upon the transplantation of these cells into a patient, may be taken up into the patient. Therefore, the addition of these factors in or on cell culture surfaces may introduce new disease even as they address an existing condition. In addition, these animal-derived additives or cell surface coatings may lead to significant manufacturing expense and lot-to-lot variability which are not preferable. There is a need for cell culture surfaces which do not include animal-derived ingredients or additives and which provide cell culture conditions amenable for cell culture, including the culture of difficult-to-culture cells such as embryonic stem cells.

SUMMARY

Embodiments of the present invention provide methods for making synthetic polymer cell culture surfaces which may be suitable for culturing difficult-to-culture cells such as embryonic stem cells.

In embodiments, the invention provides methods for making a cell culture article comprising the steps of diluting at least three (meth)acrylate monomers in a solvent wherein at least one of the at least two (meth)acrylate monomers has an N-hydroxysuccinimide moiety; dispersing the diluted monomers on a surface of a cell culture substrate; removing about 80% or more of the solvent; and polymerizing the monomers on the surface of the cell culture substrate after removing the about 80% or more of the solvent to form a synthetic polymer layer having N-hydroxysuccinimide moieties on the surface of the cell culture substrate; and, conjugating a cell adhesive peptide to the synthetic polymer layer through the N-hydroxysuccinimide moieties. In embodiments, the at least two (meth)acrylate monomers comprise at least one hydrophilic monomer, at least one cross-linker monomer and at least one conjugator monomer. In further embodiments, the conjugator monomer has an N-hydroxysuccinimide moiety, the hydrophilic acrylate monomer comprises 2-hydroxyethyl methacrylate, glycerol monomethacrylate or combinations of these and the cross-linker comprises triglycerol diacrylate, 3-(acryloyloxy)-2-hydroxypropyl methacrylate or tetraethylene glycol dimethacrylate or combinations of these.

In additional embodiments, the conjugator comprises acrylic acid N-hydroxysuccinimide ester, 2-carboxyethylacrylate N-hydroxysuccinimide ester, mono-(2-methacryoyloxyl)-ethyl succinate N-hydroxysuccinimide ester, acryl-poly ethylene glycol succinimide 3400, or combinations of these. In additional embodiments, the conjugator comprises mono-(2-methacryoyloxyl)-ethyl succinate N-hydroxysuccinimide ester. In an embodiment, the (meth)acrylate monomers comprise 2-hydroxyethyl methacrylate, acrylic acid N-hydroxysuccinimide ester and tetraethylene glycol dimethacrylate. In an embodiment, the (meth)acrylate monomers comprise 2-carboxyethylacrylate N-hydroxysuccinimide ester, 2-hydroxyethyl methacrylate and tetraethylene glycol dimethacrylate. In an embodiment, the (meth)acrylate monomers comprise mono-(2-methacryoyloxyl)-ethyl succinate N-hydroxysuccinimide ester, hydroxyethylmethacrylate and tetraethylene glycol dimethacrylate. In an embodiment, the (meth)acrylate monomers comprise acryl-poly ethylene glycol succinimide—3400, 2-hydroxyethyl methacrylate and tetraethylene glycol dimethacrylate.

In embodiments, the solvent may be alcohol or a lower alcohol. In embodiments, the dilution step further comprises diluting a UV cross-linker in the solvent. In embodiments the UV cross-linker is Darocur 1173 or Irgacure 819. In embodiments, the peptide comprises KGGNGEPRGDTYRAY (SEQ ID NO:1). In further embodiments, the invention provides a peptide-conjugated synthetic polymer cell culture surface comprising: a polymer prepared from at least three monomers, a hydrophilic monomer, a conjugator monomer and a cross-linker monomer, conjugated to a peptide; wherein the hydrophilic monomer is 2-hydroxyethyl methacrylate (HEMA), glycerol monomethacrylate or glycerol dimethacrylate, wherein the conjugator monomer is acrylic acid N-hydroxysuccinimide ester (AA-NHS), 2-carboxyethylacrylate N-hydroxysuccinimide ester (CEA-NHS), mono-(2-methacryoyloxyl)-ethyl succinate N-hydroxysuccinimide ester (MOES-NHS) or Acryl-PEG-SCM-3400, and wherein the cross-linker monomer is glycerol 1,3-diglycerolate diacrylate (TDGDDA), 3-acryloyloxy)-2-hydroxypropyl methacrylate (AHPMA) or tetraethylene glycol dimethacrylate. (TEGDMA). Embodiments provide the peptide-conjugated synthetic polymer cell culture surface having a hydrophilic monomer which is 2-hydroxyethyl methacrylate (HEMA), a conjugator monomer which is 2-carboxyethylacrylate N-hydroxysuccinimide ester and a cross-linker monomer which is tetraethyleneglycol dimethacrylate. In an embodiment, the hydrophilic monomer is 2-hydroxyethyl methacrylate (HEMA), the conjugator is mono-(2-methacryoyloxyl)-ethyl succinate N-hydroxysuccinimide ester and the cross-linker monomer is tetraethyleneglycol dimethacrylate. In embodiments, the peptide comprises KGGNGEPRGDTYRAY (SEQ ID NO:1).

DETAILED DESCRIPTION

Figure 1A:
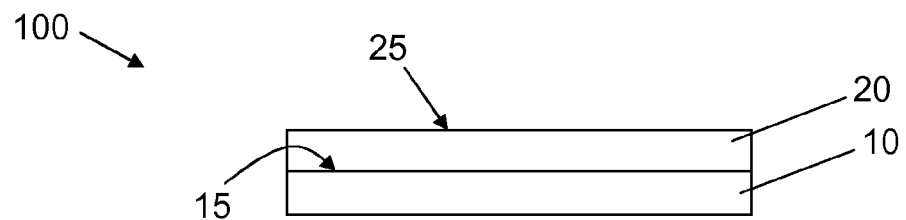
FIGS. 1A-C are schematic diagrams of side views of synthetic polymer layer coated articles.

Embodiments of the present invention include synthetic polymer surfaces which provide cell culture surfaces suitable for culturing cells including difficult-to-culture cells such as embryonic stem cells. In embodiments, (meth)acryate monomers used to create cell culture surfaces include hydrophilic monomers, reactive N-hydroxysuccinimide (NHS) acrylate monomers to conjugate polypeptides to the synthetic polymer surface (conjugator monomers), and cross-linking monomers. In additional embodiments, alternative methods for making cell culture surfaces are provided. In previously disclosed methods, monomers used to make cell culture surfaces included carboxyl functionalized acrylate monomers which were formulated into a synthetic polymer surface and later activated by N-hydroxysuccinimide (NHS) before peptide conjugation. This required the use of solvents (such as, for example N,N-dimethyl formamide, DMF). In embodiments of the present invention, NHS modification of the carboxyl in solution prior to formulating polymeric cell culture surfaces eliminates the need for a step in the manufacturing process, the NHS surface activation step, which reduces waste streams and eliminates the need for toxic solvents. In addition to the reduction in the number of steps in the method, using these monomers may reduce the use of excess reagents and solvents previously required for activation and washing of the surface. For example, in embodiments, the concentration of peptide used may decrease. In embodiments, these new monomers and methods may enable a cost effective and easily scalable method to reduce the number of processing steps for preparing the cell culture surfaces. In addition, in embodiments, these new monomers may improve the conjugation efficiency of the present formulation and derivatives thereof. In addition, these NHS acrylate monomers may be used in broader applications to attach other bioactive molecules including proteins and peptides for other applications.

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "monomer" means a compound capable of polymerizing with another monomer, (regardless of whether the "monomer" is of the same or different compound than the other monomer), which compound has a molecular weight of less that about 1000 Daltons. In many cases, monomers will have a molecular weight of less than about 400 Daltons.

As used herein, "hydrophilic monomer" means monomers that form a surface which has a low contact angle. In embodiments of the present invention, synthetic polymer surfaces made from monomers and combinations of monomers which were more hydrophilic provided improved surfaces for cell growth.

As used herein, "conjugator monomer" means an NHS functionalized (meth)acrylate monomer which can be used to conjugate a peptide (polypeptide, protein or other bioactive compound) to a surface. In embodiments the surface is a synthetic polymer surface.

As used herein, "cross-linker monomer" means monomers which have more than one polymerization moiety which can form a bond with another monomer to form a cross-link. In embodiments, the polymerization moiety may be (meth)acrylate moieties. The higher the percentage of cross-linking monomers in a mixture, the more cross-linked the cell culture surface will be. More cross-linked surfaces are harder surfaces. These hard surfaces are less likely to absorb water. If they are charged monomers, they may provide good wetability, and therefore high measured modulus while at the same time, these surfaces may be hard, non-porous surfaces. Highly crosslinked surfaces are not hydrogels. That is, they do not absorb liquid. These surfaces because of their physical properties outlined may also adsorb small and large biomolecules present in the cell culture media and or proteins produced during cell growth which may further enhance growth and proliferation of cells including stem cells on the surface. In addition, cross-linker monomers can be hydrophilic. For example glycerol-1,3-diglycerolate diacrylate and 3-(acryloyloxy)-2-hydroxypropyl methacrylate are hydrophilic crosslinkers. For example, glycerol monomethacrylate is more hydrophilic than 2-hydroxyethyl methacrylate (HEMA).

As used herein, "cyclic olefin copolymer" means a polymer formed from more than one monomer species, where at least one of the monomer species is a cyclic olefin monomer and at least one other monomer species is not a cyclic olefin monomer species. In many embodiments, cyclic olefin copolymers are formed from ethylene and norbornene monomers. Cyclic olefin copolymer resins are commercially available with trade name of TOPAS® from Boedeker Plastics, Inc.

Unless stated otherwise, ratios of compounds in a composition, such as a solution, are stated on a by volume basis.

As used herein, "have", "having", "include", "including", "comprise", "comprising" or the like are used in their open ended sense, and generally mean "including, but not limited to".

The present disclosure describes, inter alia, articles for culturing cells, methods for producing articles for cell culture and methods for screening surfaces for their ability to support cultured cells. Various embodiments presented herein provide for the ability to produce uniform, non-toxic synthetic polymer coatings for use in high throughput screening to identify synthetic coatings that provide favorable interactions with cultured cells.

(Meth)acrylate monomers and combinations of (meth)acrylate monomers have been shown to support embryonic stem cells in culture (see application Ser. Nos. 12/362,782 and 12/362,924, both filed 30 Jan. 2009, and incorporated herein by reference in their entirety to the extent that it does not conflict with the present disclosure). Embryonic stem cells (ESCs), including human embryonic stem cells (hESCs), are able to grow and self-renew unlimitedly; they can be propagated in culture for extended periods and have an ability to differentiate to multiple cell types. However, these cells have specific cell culture needs. Slight changes in culture conditions can cause these cells to differentiate, or exhibit reduced growth and propagation characteristics. In many cases, ESC cultures require the addition of animal-derived materials either in or on a cell culture surface to effectively grow in culture. These animal-derived materials may harbor pathogens such as infective proteins and viruses, including retroviruses. Although some substrates have demonstrated the ability to facilitate proliferation of ESC in both un-differentiated (pluripotent) and differentiated states, they may still be considered inadequate for cell cultures that are directed toward the development of cell therapeutics in humans because of the threat of pathogens that might be carried from an animal source of cell culture additives to the cultured cells, to an individual treated with those cells. In addition, these animal-derived surfaces may have high lot-to-lot variability making results less reproducible, and they may be very expensive. In light of these disadvantages, surfaces that include animal-derived materials may be relegated to academic and pre-clinical research and may not be useful to produce, for example, stem cells to treat patients. Furthermore, because of the costs associated with these animal derived surfaces, they are considered very expensive even for academic research, leaving the door open for cheaper and safer alternatives. Therefore, to provide a product which eliminates the risks associated with animal derived products, synthetic (meth)acrylate surfaces with special surface attributes, and improved methods of making these surfaces are proposed.

In embodiments, cell culture surfaces may be made from ingredients which are not animal-derived, may sustain at least 15 passages of cells in cell culture, may be reliable and reproducible, and may allow for the growth of cells which show normal characteristics, normal karyotype, after defined passages. Cell culture surfaces for stem cells may be made from ingredients which are not animal-derived, and sustain undifferentiated growth of ES cells for at least 10 passages in culture. In embodiments, cell culture surfaces may also be stable. Cell culture surfaces may be non-toxic. They may be able to withstand processing conditions including sterilization, possess adequate shelf life, and maintain quality and function after normal treatment. In addition, preferable cell culture surfaces may be suitable for large-scale industrial production. They may be scalable and cost effective to produce. The materials may also possess chemical compatibility with aqueous solutions and physiological conditions found in cell culture environments.

Cell culture studies conducted on synthetic surfaces have demonstrated that surface properties of substrates can affect the success of cell culture and can affect characteristics of cells grown in culture. For example, surface properties can elicit cell adhesion, spreading, growth and differentiation of cells. Research conducted with human fibroblast cells 3T3 and HT-1080 fibrosarcoma cells has shown correlation with surface energetics, contact angle, surface charge and modulus (Altankov, G., Richau, K., Groth, T., The role of surface zeta potential and substratum chemistry for regulation of dermal fibroblasts interaction, Mat.-wiss. U. Werkstofftech. 2003, 34, 12, 1120-1128.) Anderson et al (2005/0019747) disclosed depositing microspots of (meth)acrylates, including polyethylene glycol (meth)acrylates, onto a substrate as surfaces for stem cell-based assays and analysis. Self-Assembled Monolayers (SAMS) surfaces with covalently linked laminin adhesive peptides have been used to enable adhesion and short-term growth of undifferentiated hES cells (Derda, S., Li, Lingyin, Orner, B. P., Lewis, R. L., Thomson, A. J., Kiessling, L. L., Defined Substrates for Human Embryonic Stem Cell Growth Identified from surface Arrays, ACS Chemical Biology, Vol. 2, No. 5, May 2, 2007, pp 347-355.

In embodiments of the present invention, polymeric surfaces composed of cross-linked blends of (meth)acrylate monomers that impart specific physical and chemical attributes to the surface, and methods of making these surfaces are provided. These specific physical and chemical attributes may facilitate the proliferation difficult-to-culture cells such as undifferentiated hESCs in embodiments of the present invention. These (meth)acrylate surfaces are made from monomers with different properties. The monomers have particular characteristics which, when combined and polymerized or cross-linked, provide (meth)acrylate surfaces that are amenable for cell culture. These characteristics may include hydrophilicity or hydrophobicity, positive charge, negative charge or no charge, and compliant or rigid surfaces. For example, monomers or combinations of monomers which are hydrophilic may provide cell culture surfaces that are preferable in embodiments of the present invention. Or, monomers or combinations of monomers which carry a charge may be preferable in embodiments of the present invention. Or, monomers or combinations of monomers which fall within a certain range of modulus or hardness may be preferable in embodiments of the present invention. Or, monomers or combinations of monomers which exhibit a combination of these attributes may be preferable in embodiments of the present invention.

Surfaces for cell culture can be described according to their characteristics such as hydrophobicity, hydrophilicity, surface charge or surface energy, wettability or contact angle, topography, modulus which describes the surface's stiffness versus compliance, degree of cross-linking of polymers, as well as chemical characteristics such as the surface expression of active chemical moieties such as oxygen or nitrogen.

In embodiments, reactive NHS-acrylate monomers (conjugator monomers) for the preparation of peptide-conjugated synthetic polymer surfaces are provided. Instead of forming polymers from mixtures of monomers including carboxyl functionalized (meth)acrylate monomers which are later surface activated by N-hydroxysuccinimide before peptide conjugation, in embodiments of the present invention, mixtures of (meth)acrylate monomers including reactive N-hydroxysuccinimide (NHS) acrylate monomers are polymerized to form synthetic polymeric cell culture surfaces. N-hydroxysuccinimide modification of the carboxyl-containing monomer in solution prior to polymerization eliminates the need for the NHS surface activation step (reducing the use of excess reagents and solvents for activation and washing of the surface). Thus, embodiments of the monomers disclosed here may enable a cost effective and easily scalable method and reduce the number of processing steps for preparing the synthetic polymeric cell culture surfaces. In addition, these conjugator monomers may increase the peptide conjugation efficiency of formulations of embodiments of synthetic polymer cell culture surfaces of the present invention.

In embodiments of the present invention, methods of synthesizing novel reactive N-hydroxysuccinimide (meth)acrylate monomers are provided. In an embodiment, reactive N-hydroxysuccinimide acrylate monomer was synthesized by the 1-(3-dimethylaminopropyl)-3-ethyl-carbodiimide hydrochloride (EDC)— mediated esterification of mono-(2-methacryoyloxyl)-ethyl succinate (compound 1), with N-hydroxysuccinimide, yielding the corresponding N-hydroxysuccinimide ester, mono-(2-methacryoyloxyl)-ethyl succinate N-hydroxysuccinimide ester (MOES-NHS) (compound 3 of Table 1) in moderate yields and >95% purity. The resulting (compound 3 of Table 1) was a compound having the chemical formula: $C_{14}H_{17}NO_8$ and a molecular weight of 327.29. Compound 2 is named, according to IUPAC conventions, 2,5-dioxopyrrolidin-1-yl 1-{2-[(2-methylprop-2-enoyl)oxy]ethyl}butanedioate, and may also be referred to as: 2,5-dioxopyrrolidin-1-yl 2-(methacryloyloxy)ethyl succinate. For the purposes of this disclosure, this compound will be referred to as mono-(2-methacryoyloxyl)-ethyl succinate N-hydroxysuccinimide ester or MOES-NHS.

In an additional embodiment, a reactive NHS-acrylate monomer was synthesized by the 1-(3-dimethylaminopropyl)-3-ethyl-carbodiimide hydrochloride (EDC)— mediated esterification of 2-carboxyethyl acrylate with NHS, yielding the corresponding NHS ester (Compound 2 of Table 1). Compound 2 of Table 1 is, according to IUPAC naming conventions, 4-(2,5-dioxopyrrolidin-1-yl)-3-oxobutyl prop-2-enoate. This compound may also be called 4-(2,5-dioxopyrrolidin-1-yl)-3-oxobutyl acrylate or 2-carboxyethylacrylate N-hydroxysuccinimide ester (CEA-NHS). This compound was made in moderate yields and >95% purity. The resultant compound had a chemical formula $C_{10}H_{11}NO_6$ and a molecular weight of 241.20. For the purposes of this disclosure, this compound will be referred to as 2-carboxyethylacrylate N-hydroxysuccinimide ester or CEA-NHS.

The reactive NHS acrylate monomers (Compounds 2 and 3 of Table 1) were subsequently UV cured, each with hydrophilic monomers and crosslinkers, to create synthetic polymer coated surfaces. Bioactivity was measured by a high throughput (HT) 1080 cell adhesion assay, followed by proof of concept for undifferentiated hESCs.

Of course one skilled in the art of synthetic organic chemistry could generate new moderate chain length NHS acrylate or acrylamide monomers that are similar to compounds 2 and 4. For example, by a two step reaction, a "polymerizable" acrylate or methacrylate group can be introduced to a primary alcohol or amine group of a short chained compound that has both carboxylic acid and amine or carboxylic acid and alcohol groups (with the carboxylic acid group protected or unprotected) and further derivatized with N-hydroxysuccinimide. Reagents suitable for introducing the acrylate group include acryloyl chloride or (meth)acryloyl chloride, acrylic anhydride or methacrylic anhydride or derivatives thereof. Examples of short chained compounds that have both carboxylic acid and amine or carboxylic acid and alcohol groups include 6-aminohexanoic acid, L-canavanine, 4-amino-3-phenyl-butyric acid, diaminobutanoic acid derivatives such as Z-Dab-OH, (N-Boc-β-amino)-Alanine-OH, (S)-(+)-2-amino-3-(2-aminoethoxy)propanoic acid monohydrochloride, 2-amino-2-norbornanecarboxylic acid. Additionally, branched or hyperbranched versions of the NHS-acrylate monomers could be similarly synthesized from amino acids such as lysine or polylysine, and branched compounds such as poly(glutamic acid) or NaNa-bis(carboxymethyl)-L-lysine hydrate.

In embodiments, methods of making these surfaces may provide improvements in the cost and expense of manufacturing polymeric or synthetic cell culture surfaces. For example, improved methods may require fewer steps or take less time, require fewer raw materials, require less toxic ingredients or create less toxic by-products, or provide better surfaces, than previously disclosed methods.

1. Cell Culture Article

Referring to FIG. 1, a schematic diagram of article 100 for culturing cells is shown. The article 100 includes a cell culture substrate or base material substrate 10 having a surface 15. A synthetic polymer coating layer 20 is disposed on the surface 15 of the cell culture substrate or base material 10. While not shown, it will be understood that synthetic polymer coating 20 may be disposed on a portion of cell culture substrate or base material 10. The cell culture substrate or base material 10 may be any material suitable for culturing cells, including ceramic, glass, glass-ceramic, metal, plastic, polymer or co-polymer, any combinations thereof, or a coating of one material on another. Such base materials 10 include glass materials such as soda-lime glass, pyrex glass, vycor glass, quartz glass, or the like. For example, substrates may be gas permeable or gas impermeable polymeric substrates or membranes made of suitable materials that may include for example: polystyrene, polyethylene, polyethyleneterephthalate, polyethylene-co-vinyl acetate, nylon, polycarbonate, polyolefin, ethylene vinyl acetate, polypropylene, polysulfone, polytetrafluoroethylene (PTFE) or compatible fluoropolymer, silicone rubber or copolymer, poly(styrene-butadiene-styrene), dendritic polymers, such as poly(vinyl chloride), poly(vinyl alcohol), poly(methyl methacrylate), poly(vinyl acetate-maleic anhydride), poly(dimethylsiloxane) monomethacrylate, cyclic olefin polymers, fluorocarbon polymers, polystyrenes, polypropylene, polyethyleneimine; copolymers such as poly(vinyl acetate-co-maleic anhydride), polystyrene-co-maleic anhydride), poly(ethylene-co-acrylic acid) or derivatives of these or the like.

The substrate may be treated to alter the surface characteristics of the substrate in order for surfaces to facilitate sustainable adhesion between thermoplastic substrates and said (meth)acrylate components. For example, the substrate may be plasma treated, chemically treated, heat treated, mechanically etched, or have increased charged chemical groups available at the surface of the polymer substrate in which (meth)acrylate coating is to be applied.

In an embodiment, the substrate may be a plasma-treated polystyrene, polyolefin or cyclic olefin co-polymer surface. The plasma-treated cyclic olefin co-polymer (cyclic norbonene-ethylene) surface may be, for example, that material sold under the name of TOPAS® by Topas Advanced Polymers, Florence, Ky. In embodiments, dispursing the (meth)acrylate monomer mixture on a substrate can be done using methods known in the art, including dip coating, spray coating, spin coating, or liquid dispensing. For example, a liquid monomer mixture can be applied to a surface and the surface can be tilted to distribute the mixture over the surface.

In embodiments, the substrate may form part of a cell culture article. Cell culture articles 100 are containers suitable for containing cells in culture. Cell culture articles include flasks, bottles, plates, single and multi-well plates such as 6, 12, 96, 384, and 1536 well plates, multi-layer flasks, jars, dishes, beakers, roller bottles, slides including chambered and multi-chambered culture slides, tubes, cover slips, membranes, cell culture container inserts, beads, fibers, hollow fibers, bags, bioreactors, fermenters, perfusion chambers, cups, spinner flasks, spinner bottles, and/or any type of cell culture vessel or container known in the art.

While all sizes are contemplated, in embodiments of the present invention, the (meth)acrylate cell culture surface covers a surface of the cell culture article that is larger than a small spot, or microspot, or larger than 1000 µm in diameter, in the cell culture article. In embodiments, the (meth)acrylate cell culture surface of the present invention covers an entire cell culture surface in the cell culture container or vessel. For example, in embodiments, the (meth)acrylate cell culture surface of the present invention covers the bottom, the cell culture growth surface, of a well of a 96-well plate. Or, in embodiments, the cell culture surface of the present invention covers the cell culture growth surface of a standard cell culture flask. Those of ordinary skill will recognize that embodiments of the present invention may provide cell culture surfaces for known cell culture vessels and containers. Synthetic polymer coating 20 provides a surface 25 on which cells may be cultured or screened. Synthetic polymer coating may be referred to as synthetic polymer layer, synthetic polymer coating, synthetic polymer surface synthetic surface or any other suitable term. In numerous embodiments, synthetic polymer surface 20 is formed of polymerized (meth)acrylate monomers. Of course synthetic polymer surface 20 may be formed from any other suitable class of biocompatible polymers such as polyamides, polyphosphazenes, polypropylfumarates, synthetic poly(amino acids), polyethers, polyacetals, polycyanoacrylates, polyacrylamides, polyurethanes, polycarbonates, polyanhydrides, poly(ortho esters), polyhydroxyacids, polyesters, ethylene-vinyl acetate polymers, cellulose acetates, polystyrenes, poly(vinyl chloride), poly(vinyl fluoride), poly(vinyl imidazole), poly(vinyl alcohol), chlorosulphonated polyolefins, and combinations thereof or combinations thereof with poly(meth)acrylates. In various embodiments, synthetic polymer layer 20 is a (meth)acrylate layer.

Regardless of the monomers used, the properties of the resulting polymers may be adjusted. For example, ester and ether groups, to different degrees, contribute to the hydrophilicity of the resulting polymer, and thus the amounts of such groups can be varied to vary hydrophilicity. In addition, the use of amino, thio, or oxygenated groups may be employed in desired amounts to vary the electron density of the resulting polymer. Further, by varying the number of ether groups in the monomer and the distance between the ester linkages, the electron density of the polymer may be readily tailored. Branched monomers also change electron density by allowing more ether groups to fit in a certain length or by changing the packing density of the resulting polymer. The use of cyclic moieties and aromatic moieties also affects electron density. In addition, the cross-link density of the polymer may be adjusted by varying the proportion of multifunctional, such as bi- or tri-functional monomers to monofunctional monomers.

The molecular weight of the polymer may be controlled by varying the concentration of monomer in the stock solution or the ratios of difunctional or higher-functional monomers to monofunctional monomers. Increased concentrations of difunctional or higher-functional monomers will increase the degree of cross-linking in the chains. Monofunctional monomers may be modified to form difunctional monomers by reacting them with a linker chain. Appropriate linkers and chemical reactions will be evident to one skilled in the art. For example, dicarboxylic acids are reactive with a wide variety of functional groups commonly incorporated into vinyl monomers, including alcohols, amines, and amides.

In some embodiments, (meth)acrylate layer is formed from a hydrophilic monomer, a carboxyl group containing monomer which has been derivatized by attaching an N-hydroxysuccinimide group (NHS) (a conjugator monomer), and a crosslinking monomer. In embodiments, the conjugator monomer may comprise any chemical moiety which is suitable for (1) forming a polymer alone or in combination with other monomers; and (2) conjugating a bioactive compound such as a peptide (or polypeptide) to the formed polymer. In embodiments, the N-hydroxysuccinimide group may be attached to a monomer by any chemical moiety suitable for attaching an N-hydroxysuccinimide group to form a conjugator monomer. In embodiments, the carboxyl group containing monomer which has been modified to attach an N-hydroxysuccinimide group (NHS) is a conjugator monomer.

In embodiments, examples of hydrophilic monomers include 2-hydroxyethyl methacrylate (HEMA) or glycerol monomethacrylate (mixed isomers) (structures shown in Table 1). Examples of an N-hydroxysuccinimide modified carboxyl group containing monomer include, for example, acrylic acid N-hydroxysuccinimide ester (AA-NHS), 2-carboxyethylacrylate N-hydroxysuccinimide ester (CEA-NHS), mono-(2-methacryoyloxyl)-ethyl succinate N-hydroxysuccinimide ester or Acryl-Peg-SCM-3400 (available from Laysan Bio. Inc. Arab, Ala.) (structures shown in Table 2). Examples of cross-linking monomers include, for example, triglycerol diacrylate (glycerol 1,3-diglycerolate diacryate—TDGDDA), 3-(acryloyloxy)-2-hydroxypropyl methacrylate (AHPMA), or tetraethylene glycol dimethacrylate (TEGDMA) (structures shown in Table 3). In an embodiment, a (meth)acrylate layer may be formed from 2-hydroxyethyl methacrylate, tetraethylene glycol dimethacrylate and 2-carboxyethylacrylate N-hydroxysuccinimide ester (CEA-NHS). In an additional embodiment, the synthetic polymer layer is formed from 2-hydroxyethyl methacrylate, tetraethylene glycol dimethacrylate and mono-(2-methacryoyloxyl)-ethyl succinate N-hydroxysuccinimide ester (MOES-NHS). Of course, any other suitable (meth)acrylate monomer may be used. One or more (meth)acrylate monomer is used to form the synthetic polymer layer. Many (meth)acrylate polymers are commercially available from, e.g., Polysciences, Inc., Sigma Aldrich, Inc., and Sartomer, Inc. In various embodiments, the synthetic layer is formed from a composition comprising one or more (meth)acrylate monomers, where at least one of the one or more monomers is glyceryl monomethacrylate or glycerol dimethacrylate.

TABLE 1

Conjugator Monomers

| Compound number | Structure | Name |
|---|---|---|
| 1 | 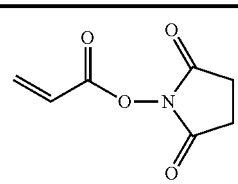 | acrylic acid N-hydroxysuccinimide ester (AA-NHS) |
| 2 | 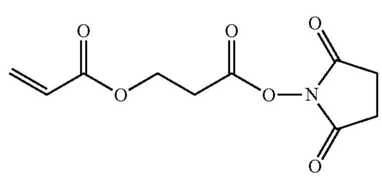 [SMILES: C=CC(=O)OCCC(=O)ON1C(=O)CCC1=O] | 2-carboxyethylacrylate N-Hydroxysuccinimide ester (CEA-NHS) |
| 3 | 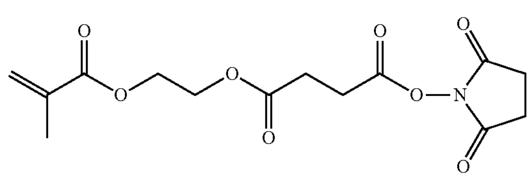 [SMILES: C=C(C)C(=O)OCCOC(=O)CCC(=O)ON1C(=O)CCC1=O] | mono-(2-methacryloyloxyl) ethylsuccinimide ester (MOES-NHS) |
| 4 | 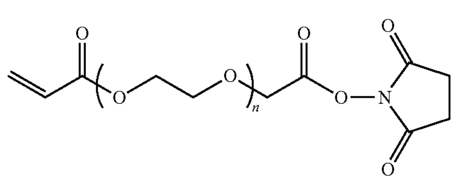 | Acryl-Peg-SCM-3400 |

TABLE 2

Hydrophilic Monomers

| Compound number | Structure | Name |
|---|---|---|
| 5 | 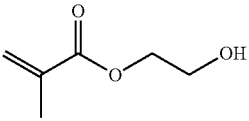 | 2-hydroxyethyl acrylate (HEMA) |
| 6 | 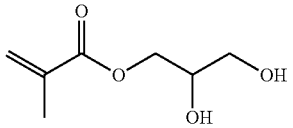<br />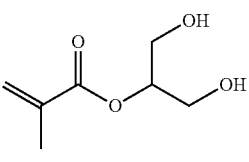 | glycerol monoethacrylate (mixed isomers) (GMMA) |

TABLE 3

Crosslinker Monomers

| Compound number | Structure | Name |
|---|---|---|
| 7 | 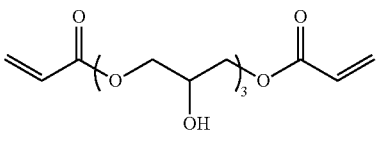 | triglycerol diacrylate (glycerol 1,3-diglycerolate diacryate) (TDGDDA) |
| 8 | 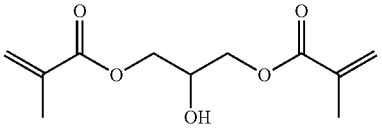 [SMILES: C=C(C)C(=O)OCC(O)COC(=O)C(=C)C] | 3-(Acryloyloxy)-2-hydroxypropyl methacrylate (AHPMA) |
| 9 | 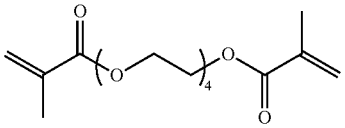 | tetraethyleneglycol dimethacrylate (TEGDMA) |

Figure 1B:
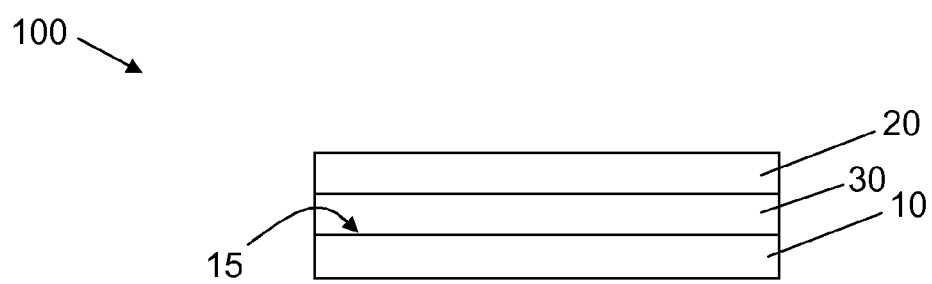

As shown in FIG. 1B, an intermediate layer 30 may be disposed between surface 15 of cell culture substrate or base material 10 and the synthetic polymer coating 20. Intermediate layer 30 may be configured to improve binding of coating 20 to substrate 10, to facilitate monomer spreading, to render portions of the cell culture surface or base material 10 that are uncoated and non-adhesive to encourage cell growth on coated areas, to provide a substrate compatible with a monomer or solvent where the monomer or solvent is incompatible with the base material 10, to provide topographical features if desired through, for example, patterned printing, or the like. For example, if substrate 10 is a glass substrate, it may be desirable to treat a surface of the glass substrate with an epoxy coating. For various polymer base materials 10 it may be desirable to provide an intermediate layer 30 of polyimide, polyimide, polypropylene, polyethylene, or poly(meth)acrylate. While not shown, it will be understood that synthetic polymer coating 20 may be disposed on a portion of intermediate layer 30. It will be further understood that intermediate layer 30 may be disposed on a portion of base material 10.

Figure 1C:
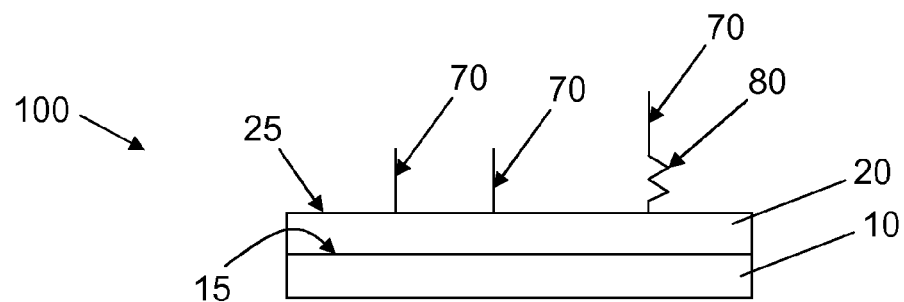

Referring now to FIG. 1C, other materials, such as bioactive compounds 70, may be incorporated into or conjugated to synthetic polymer surface 20, e.g. to produce a biomimetic surface. In embodiments, the bioactive compound is a protein, a polypeptide (or peptide). For the purposes of this disclosure, the terms polypeptide and peptide are synonymous. For example the bioactive compound may be a molecule capable of binding noncovalently to specific and complimentary portions of molecules or cells. Examples of such bioactive compounds include cell surface receptors which bind to ligands, antigens which bind to antibodies.

In embodiments, larger proteins may be conjugated to synthetic polymer surface. Proteins may include both animal derived or non-animal derived recombinant proteins. Recombinant proteins may be sourced from bacterial plasmid expression systems, eukaryotic expression systems such as baculovirus. It is also contemplated that protein-sourcing from cell-free expression systems such as the RTS Wheat germ cell-free synthesis process (available from Roche Inc.) may also be applied.

In additional embodiments, larger proteins may be conjugated to the pre-activated derivatized surface. In embodiments, large proteins may be conjugated to the derivatized surface in aqueous conditions, in a manner analogous to the Examples provided herein. Alternatively, one can also use hapten binding retention of hapten tagged proteins. It is know in the art that biotinylated proteins can be retained with high selectivity via Streptavidin and Avidin complexes. A protein may be tagged with biotin by either chemical or enzymatic processes. The AviTag® process by GeneCopoeia Inc. involves fusion of a biotin linker using biotin ligase.

In embodiments, the protein to be attached may be extracellular matrix proteins, such as, for example, Collagen Type I, II, III, IV, V, VI, VII, VIII, Fibronectin, vitronectin, Laminin a, b and c chains Enactin, Elastin and any other ECM proteins. Glycoproteins and growth factors may also be attached to the synthetic polymer surface.

In embodiments, the bioactive compound is conjugated to the synthetic polymer surface 20 via the NHS-moiety of the conjugator monomer (for example, compounds 2 and 3 from Table 1). In various embodiments where bioactive compounds 70 are conjugated to synthetic polymer surface 20, synthetic polymer surface 20 is a hydrogel layer or a swellable (meth)acrylate layer. A linker or spacer 80, such as a repeating polyethylene glycol linker or any other suitable linker, may be conjugated to the NHS moiety of the conjugator monomer, and then attached to a polypeptide. In embodiments, the linker or spacer may be used to increase distance from polypeptide 70 to surface 25 of synthetic polymer layer 20. All, some, or none of the polypeptides 70 may be conjugated to synthetic polymer layer 20 via linkers 80.

Bioactive compound 70 may be conjugated to the synthetic polymer layer 20 at any density, preferably at a density suitable to support culture of cells for a desired purpose. For example, when the bioactive compound 70 is a polypeptide, the polypeptide may be conjugated to synthetic polymer layer 20 at a density of between about 1 pmol per mm$^2$ and about 50 pmol per mm$^2$ of surface 25 of synthetic polymer layer 20, which can be estimated by the area of surface 15 of base material substrate 10 that is coated in embodiments where surface 15 is uniformly coated by synthetic polymer layer 20. For example, the polypeptide may be present at a density of greater than 5 pmol/mm$^2$, greater than 6 pmol/mm$^2$, greater than 7 pmol/mm$^2$, greater than 8 pmol/mm$^2$, greater than 9 pmol/mm$^2$, greater than 10 pmol/mm$^2$, greater than 12 pmol/mm$^2$, greater than 15 pmol/mm$^2$, or greater than 20 pmol/mm$^2$ of the surface of the synthetic polymer layer 20. It will be understood that the amount of polypeptide 70 present can vary depending on the composition of the synthetic polymer layer 20, the thickness of the synthetic polymer layer 20 and the nature of the polypeptide 70 itself.

In various embodiments, the polypeptide is derived from a naturally occurring cell adhesion polypeptide, such as fibronectin, laminin, vitronectin, or the like. For the purposes of this disclosure, cell adhesion peptide, or cell adhesion polypeptide means a peptide sequence which is known to aid in cell adhesion. In some embodiments, the polypeptide contains an RGD amino acid sequence. In embodiments, the polypeptide is KGGNGEPRGDTYRAY (SEQ ID NO:1) which is an RGD sequence from bone sialoprotein with an additional "KGG" sequence is added to the N-terminus. Lysine (K) was used for chemical conjugation, and two glycine amino acids (GG) were added as spacers. In additional embodiments Cystine (C) may be used for chemical conjugation. In embodiments, a conjugation and spacer sequence (KGG or CGG, for example) may be present or absent. In additional embodiments, the polypeptide may be, for example, NGEPRGDTYRAY, (SEQ ID NO:2), GRGDSPK (SEQ ID NO:3) (short fibronectin) AVTGRGDSPASS (SEQ ID NO:4) (long FN), PQVTRGDVFTMP (SEQ ID NO:5) (vitronectin), RNIAEIIKDI (SEQ ID NO:6) (lamininβ1), KYGRKRLQVQLSIRT (SEQ ID NO:7) (mLMα1 res 2719-2730), NGEPRGDTRAY (SEQ ID NO:8) (BSP-Y), NGEPRGDTYRAY (SEQ ID NO:9) (BSP), KYGA-ASIKVAVSADR (SEQ ID NO:10) (mLMα1 res 2122-2132), KYGKAFDITYVRLKF (SEQ ID NO:11) (mLMγ1 res 139-150), KYGSETTVKYIFRLHE (SEQ ID NO:12) (mLMγ1 res 615-627), KYGTDIRVTLNRLNTF (SEQ ID NO:13) (mLMγ1 res 245-257), TSIKIRGTYSER (SEQ ID NO:14) (mLMγ1 res 650-261), TWYKIAFQRNRK (SEQ ID NO:15) (mLMα1 res 2370-2381), SINNNRWHSIYITRFGNMGS (SEQ ID NO:16) (mLMα1 res 2179-2198), KYGLA-LERKDHSG (SEQ ID NO:17) (tsp1 RES 87-96), GQ-CIVQTTSWSQCSKS (SEQ ID NO:18) (Cyr61 res 224-240).

In additional embodiments, the peptide comprises KGGK$^4$DGEPRGDTYRATD$^{17}$ (SEQ ID NO:19), where Lys$^4$ and Asp$^{17}$ together form an amide bond to cyclize a portion of the polypeptide; KGGL$^4$EPRGDTYRD$^{13}$ (SEQ ID NO:20), here Lys$^4$ and Asp$^{13}$ together form an amide bond to cyclize a portion of the polypeptide; KGGC$^4$NGEPRGDTYRATC$^{17}$ (SEQ ID NO:21), where Cys$^4$ and Cys$^{17}$ together form a disulfide bond to cyclize a portion of the polypeptide; KGGC$^4$EPRGDTYRC$^{13}$ (SEQ ID NO:22), where Cys$^4$ and Cys$^{13}$ together form a disulfide bond to cyclize a portion of the polypeptide, or KGGAVT-GDGNSPASS (SEQ ID NO:23). In embodiments, the polypeptide may be acetylated or amidated or both. While these examples are provided, those of skill in the art will recognize that any peptide or polypeptide sequence may be conjugated to embodiments of the synthetic polymer coating of the present invention.

In various embodiments, surface 15 of base material 10 is treated, either physically or chemically, to impart a desirable property or characteristic to the surface 15. For example, and as discussed below, surface 15 may be corona treated or plasma treated. Examples of vacuum or atmospheric pressure plasma include radio frequency RF and microwave plasmas both primary and secondary, dielectric barrier discharge, and corona discharge generated in molecular or mixed gases including air, oxygen, nitrogen, argon, carbon dioxide, nitrous oxide, or water vapor.

Synthetic polymer coating layer 20, whether disposed on an intermediate layer 30 or base material 10, preferably uniformly coats the underlying substrate. By "uniformly coated", it is meant that the layer 20 in a given area, for example a surface of a well of a culture plate, completely coats the area at a thickness of about 5 nm or greater. In embodiments, while the thickness of a uniformly coated surface may vary across the surface, there are no areas of the uniformly coated surfaces through which the underlying layer (either intermediate layer 30 or base material 10) is exposed. Cell responses across non-uniform surfaces tend to be more variable than cell responses across uniform surfaces.

Synthetic polymer coating layer 20 may have any desirable thickness. However, it has been found that thicker coatings, e.g. coatings of greater than about 10 micrometers, tend to have unevenness around the periphery of the coating due to surface tension. In various embodiments, the thickness of the coating layer 20 is less than about 10 micrometers. For example, the thickness may be less than about 5 micrometers, less than about 2 micrometers, less than about 1 micrometers, less than about 0.5 micrometers or less than about 0.1 micrometers.

The polymer material forming synthetic polymer layer 20 may be cross-linked to any suitable degree. Low degree of crosslinking may result in partial or complete synthetic polymer layer dissolution and lower polymerization reaction efficiency. In various embodiments, the crosslinking density of synthetic polymer layer 20 is between about 0.9% and about 9%.

Figure 2A:
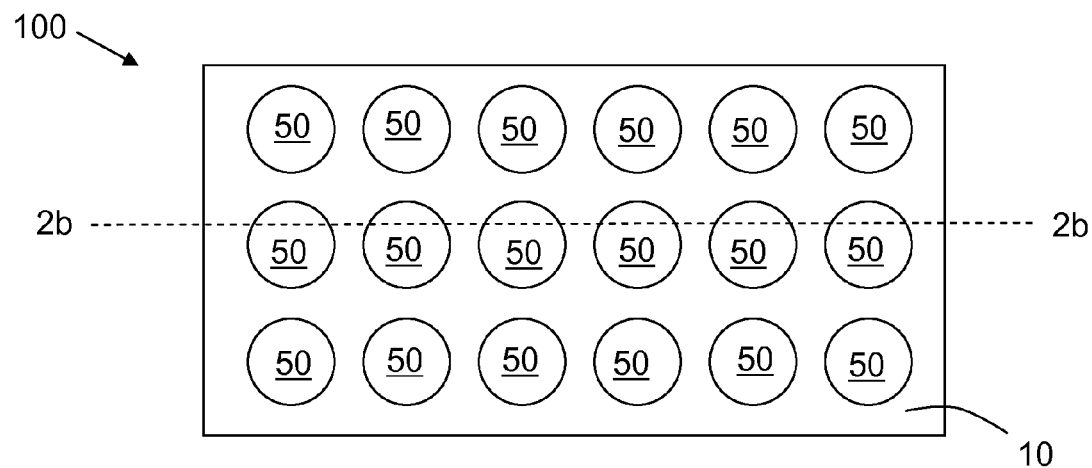
FIG. 2A is a schematic diagram of a top view of a multi-well cell culture plate.
Figure 2B:
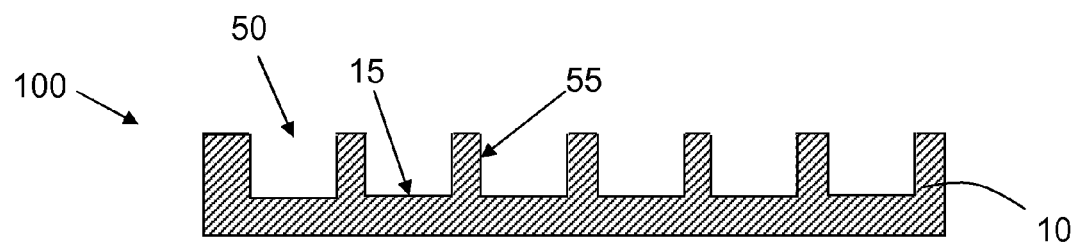
FIGS. 2B and C are schematic diagrams side views of cross sections taken through line 2*b*-2*b* of the multi-well plate depicted in FIG. 2A. The wells depicted in FIG. 2B are uncoated. The wells depicted in FIG. 2C are coated with a synthetic polymer.
Figure 2C:
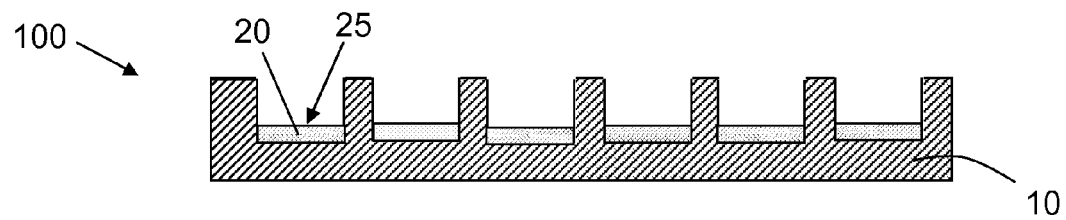

Article 100, in numerous embodiments, is traditional cell culture ware, such as a Petri dish, a multi-well plate, a slide, a flask, a multi-layer flask, a bead, a bioreactor, a bag and a beaker or other item having a surface suitable for cell culture. Referring now to FIG. 2, article 100 formed from base material 10 may include one or more wells 50. Well 50 includes a sidewall 55 and a surface 15. A synthetic polymer coating 20 may be disposed on surface 15 (or, as discussed above with regard to FIG. 1 one or more intermediate layer 30 may be disposed between surface 15 and synthetic polymer coating 20). While not shown, it will be understood that sidewall 55 may be coated with synthetic polymer layer 20. While a well is shown in FIG. 2 for illustrative purposes, it will be understood that synthetic polymer layer 20 may be on any surface suitable for cell culture.

In various embodiments, article 100 includes a uniformly coated layer 20 having a surface 25 with an area greater than about 5 mm$^2$. Of course, the surface 25 may be of any suitable size. However, when the area of the surface 15 is too small, reliable cell responses may not be readily observable because some cells, such as human embryonic stem cells, are seeded as colonies or clusters of cells (e.g., having a diameter of about 0.5 mm) and adequate surface area is desirable to ensure attachment of sufficient numbers of colonies to produce a quantitative cell response. In numerous embodiments, an article 100 has a well 50 having a uniformly coated surface 15, where the surface 15 has an area greater than about 0.1 cm$^2$, greater than about 0.3 cm$^2$, greater than about 0.9 cm$^2$, or greater than about 1 cm$^2$.

When article 100 is used for purposes of screening, article 100 preferably contains a plurality of wells 50. Different wells 50 may include synthetic polymer coating layers 20 having different thicknesses, formed from different monomers or combinations of monomers, or the like, to facilitate screening of the response of cells to the different layers 20. Of course, some wells 50 may contain no synthetic polymer layers 20 or may contain other substrates for cell culture, such as MATRIGEL™ or the like, to serve as negative or positive controls.

In embodiments, the synthetic polymer layer may be a swellable (meth)acrylate (SA) layer. In various embodiments, the synthetic polymer layer may be attached to a surface of a cell culture article. For the purposes of this disclosure, "attached" means coated on or layered on a base material or substrate so that the synthetic polymer layer does not delaminate from the base material upon exposure to normal cell culture conditions including exposure to aqueous media. The synthetic polymer layer may be attached to the substrate via covalent or non-covalent interactions. Embodiments of the present invention provide a synthetic polymer layer having N-hydroxysuccinimide moieties on the surface of a cell culture substrate. For the purposes of this disclosure "on" means disposed on a surface of a cell culture substrate by means of non-covalent or covalent interactions. Examples of non-covalent interactions that may associate the synthetic polymer surface with the substrate include chemical adsorption, hydrogen bonding, surface interpenetration, ionic bonding, Van der Waals forces, hydrophobic interactions, dipole-dipole interactions, mechanical interlocking, and combinations thereof. Examples of covalent interactions may include copolymerization of the (meth)acrylate monomers with a surface containing either a polymerizable group (e.g., acrylate), a group capable of fragmenting to produce free radical, or chain transfer agent, and combinations thereof.

For the purposes of this disclosure, the term "(meth)acrylate" means compounds that are esters which contain vinyl groups, that is, two carbon atoms double bonded to each other, directly attached to a carbonyl carbon. An acrylate moiety is a moiety of the following formula: $CH_2CHC(O)O^-$. Some acrylates, methacrylates, have an extra methyl group attached to the α-carbon and these are also included in the term "(meth)acrylate" for the purposes of this disclosure. A methacrylate moiety is a moiety of the following formula: $CH_2C(CH_3)C(O)O^-$. "acrylate" and "(meth)acrylate" are used herein interchangeably, except when content clearly dictates otherwise, e.g. when a specific compound or group of compounds are named. "(meth)acrylate" includes compounds which contain single (meth)acrylate groups or multiple (meth)acrylate groups. "(meth)acrylate" includes acrylates and methacrylates as well as polymerized and unpolymerized monomers (oligomers) with varying reactive functionality, that is, dimers, trimers, tetramers or additional polymers containing acrylic or methacrylic acid groups. "UV-curable monomers," for the purposes of this disclosure means monomers that can be cross-linked to form polymers by exposure to UV light. In addition, for the purposes of this disclosure, the term "UV-curable monomers" includes compounds described in Tables 1-3. These compounds can also possess non-reactive or reactive moieties in their backbones such as amine, carboxyl, urethane, cyanurate, glycol, diol, ring structures such as furan, imidazole, morphilino and pyrrolidone.

2. Coating of Synthetic Polymer Layer

The discussion that follows makes reference to articles 100 and components thereof as described above with regard to FIGS. 1-2. However, it will be understood that any suitable article may be employed with regard to the methods that follow.

Figure 3:
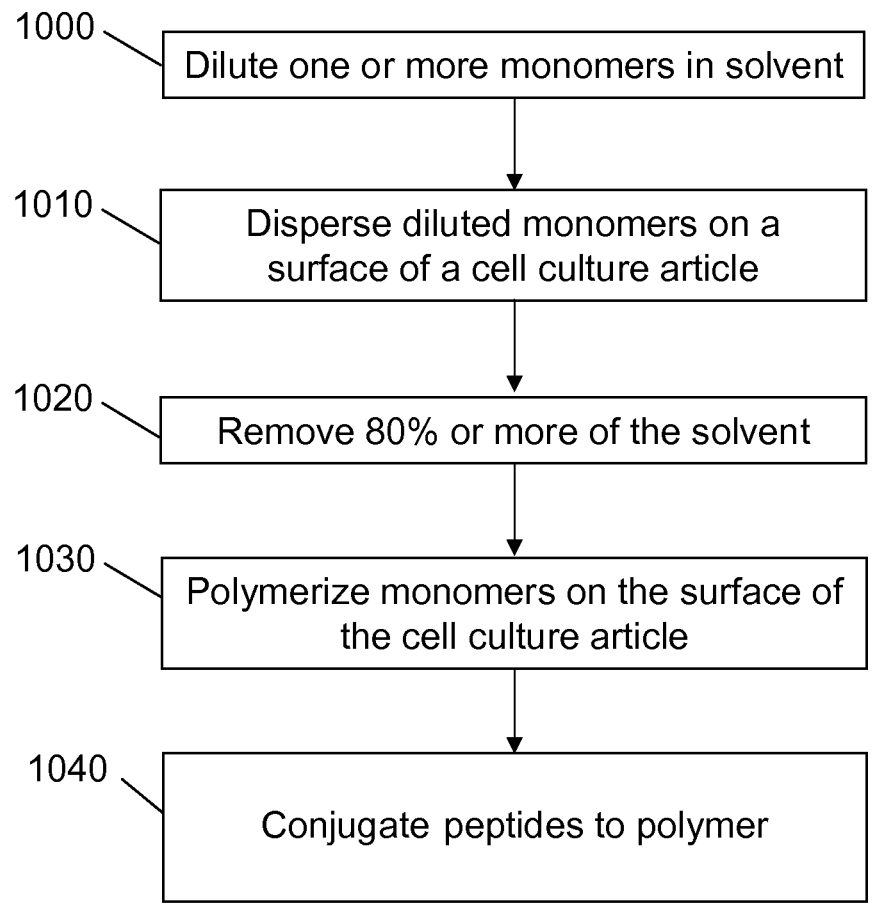
FIG. 3 is a flow diagram of representative method for producing a cell culture article having a synthetic polymer layer.
Figure 4:
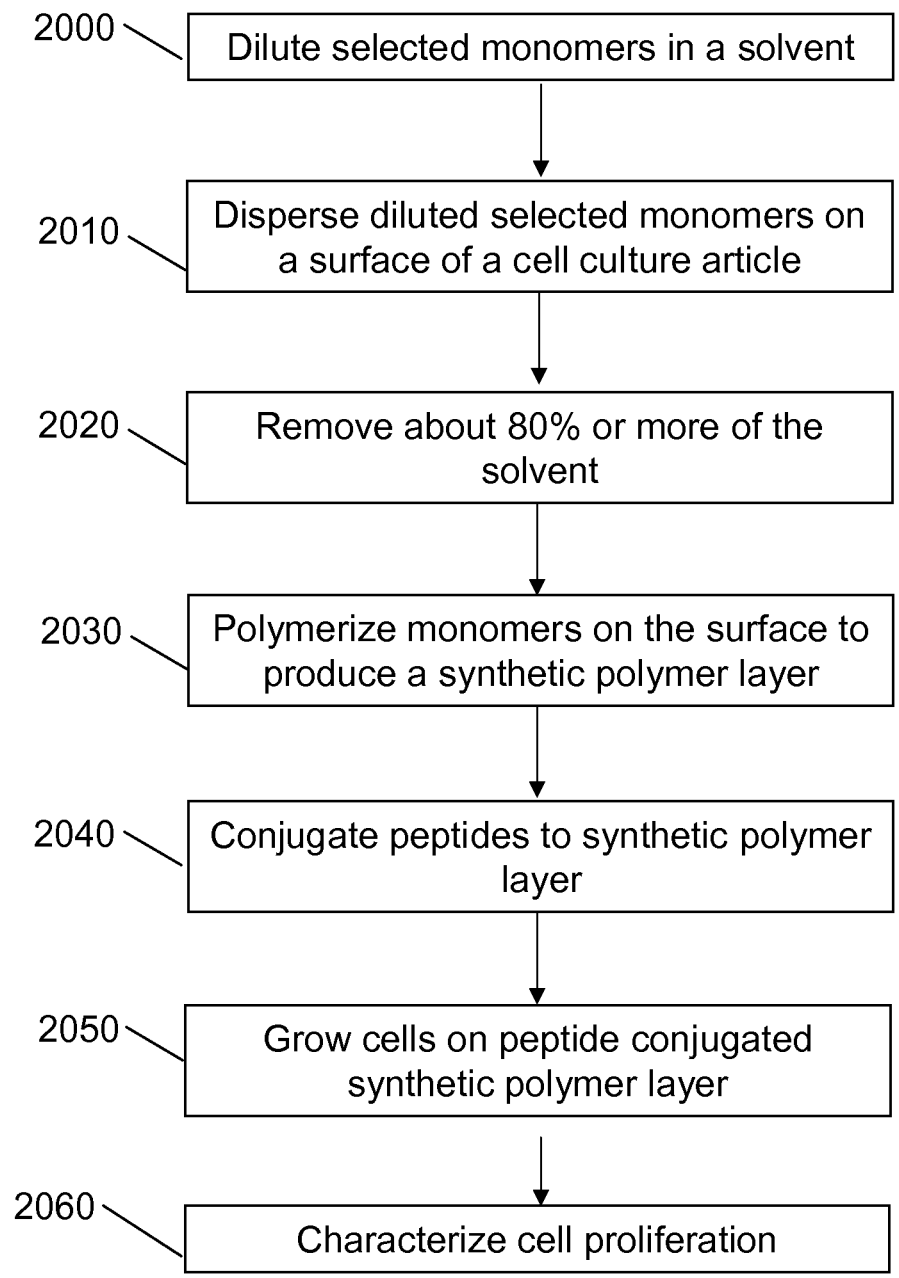
FIG. 4 is a flow diagram of a representative method for producing a cell culture article and growing cells on the cell culture article.

Referring now to FIG. 3, a flow diagram of a process for producing a cell culture article is shown. The method includes (1000) diluting one or more monomers in a solvent and (1010) dispersing the diluted monomers on a surface 15 of a cell culture article 100. About 80% or more of the solvent is then removed in step (1020). The solvent can be removed by any process known in the art, including evaporating a volatile solvent to remove the solvent. After removing the solvent the monomers are polymerized on the surface 15 of the article 100 in situ in step (1030). In some embodiments, about 90% or more, about 95% or more, about 99% or more, substantially all, or essentially all of the solvent is removed prior to polymerizing the monomers. After the monomers are polymerized in step 1030 to form polymers, peptides are conjugated to the polymers (1040). In an additional optional step, in embodiments, cells may be grown on the peptide conjugated synthetic polymer layer (1050).

Any suitable solvent may be used in the process of forming the synthetic polymer layer depicted in FIG. 3. In various embodiments, the solvent is a volatile solvent. As used herein, a volatile solvent is a solvent having a boiling point of less than about 120° C., less than about 100° C., less than about 90° C., or less than about 85° C. For example, the volatile solvent may have a boiling point between about 34° C. and about 120° C., between about 50° C. and about 100° C., or between about 70° C. and about 85° C. Examples of volatile solvents include acetone, methanol, ethyl acetate, ethanol, butanone, acetonitrile, 2-propanol, and 2-butanol. A volatile solvent preferably is readily evaporatable at room temperature, compatible with the monomers used to generate the synthetic polymer surface, non-interfering with free-radical polymerization, and non-toxic to cells to be cultured. A volatile solvent may include a non-volatile component, such as dimethyl formamide or dimethyl sulfoxide. When a volatile solvent includes a non-volatile component, the non-volatile component is preferably kept to an amount of less than about 10% by volume. A solvent used in accordance with a method as described herein is preferably a poor solvent for the base material 10 of the culture ware article 100.

A representative example of suitable class of volatile solvents is ethanol solvents. As used herein, "ethanol solvent" means a solvent having greater than about 75% ethanol. For example, an ethanol solvent may contain greater than 80%, greater than 90%, greater that 95%, greater than 97%, or greater than 99% ethanol. In various embodiments, the ethanol solvent consists essentially of ethanol. In some embodiments, an ethanol solvent consists essentially of ethanol and water. The use of an ethanol solvent may provide one or more advantages over the use of no solvent. For example, use of an ethanol solvent reduces monomer viscosity, making it possible to use automated instrumentation in the formulation process. Efficiency has been increased ten fold relative to use of no solvent, making it possible to do high throughput material screening. Use of an ethanol solvent promotes monomer spreading to achieve a thin and uniform coating for small or large surface areas using automated liquid handling instrumentation and increases coating efficiency. Use of an ethanol solvent also reduces the amount of monomer used for the coating process and may reduce final coating thickness. This can reduce cost by reducing consumption of monomers while reducing stress in coating during polymerization and swelling after contact with culture medium and finally reduces coating de-lamination. Compared to other solvents, ethanol solvents are more likely to be safe for the manufacture of cell culture ware for therapeutic cells or tissues, as ethanol solvents have been used in biomedical and pharmaceutical processes. Further, ethanol solvents are commercially available in USP grade, are easy to evaporate or otherwise remove during coating process without extreme conditions such as extreme vacuum or heat, are good solvents for a large majority of (meth)acrylate monomers while being a poor solvent for many polymers used in cell culture ware base material. In addition, ethanol appears to be relatively inert during free radical polymerization. Therefore, side effects of an ethanol solvent on the subsequent polymerization of the coating have been found to be minimal. 2-propanol solvents share many of the above-described advantages of ethanol solvents.

The monomers may be diluted with solvent by any suitable amount to achieve the desired viscosity and monomer concentration. Generally the monomer compositions used according to the teachings presented herein contain between about 0.1% to about 99% monomer. By way of example, the monomer may be diluted with an ethanol solvent to provide a composition having between about 0.1% and about 50% monomer, from about 0.01% to about 10% monomer by volume, from about 0.1% to about 5% monomer by volume, or from about 0.1% to about 1% monomer by volume. The monomers may be diluted with solvent so that the polymer layer 20 achieves a desired thickness. As discussed above, if the deposited monomers are too thick, a non-uniform surface may result and the coating may likely de-laminate after contact with an aqueous medium. As described in further details in the Examples, non-uniform surfaces may be observed when the monomer-solvent composition is deposited on a surface 15 of a well 50 at a volume of greater than about 8 microliters per square centimeter of the surface 15. In various embodiments, the monomer-solvent compositions are deposited on a surface 15 of a well 50 in a volume of about 15 microliters or less per square centimeter of the surface 15. For example, the monomer-solvent compositions may be deposited on a surface 15 of a well 50 in a volume of about 7 microliters or less per square centimeter of the surface 15, or about 3 microliters or less per square centimeter of the surface 15.

In various embodiments, synthetic polymer surface 20 is produced by depositing or dispersing one or more monomers on a surface 15 of a base material 10 and then polymerizing the one or more monomers in situ. In such embodiments, the base material 10 will be referred to herein as the "substrate" on which the synthetic polymer material 20 is deposited. The synthetic polymer surface 20 may be associated with the base material surface 15 via covalent or non-covalent interactions. Examples of non-covalent interactions that may associate the synthetic polymer surface with the substrate include chemical adsorption, hydrogen bonding, surface interpenetration, ionic bonding, Van der Waals forces, hydrophobic interactions, dipole-dipole interactions, mechanical interlocking, and combinations thereof. Examples of covalent interactions may include copolymerization of the (meth)acrylate monomers with a surface containing either a polymerizable group (e.g., acrylate), a group capable of fragmenting to produce free radical, or chain transfer agent, and combinations thereof.

In various embodiments, synthetic polymer surface 20 is deposited on a surface of an intermediate layer 30 that is associated with the base material 10 via covalent or non-covalent interactions, either directly or via one or more additional intermediate layers (not shown). In such embodiments, the intermediate layer 30 will be referred to herein as the "substrate" onto which the synthetic polymer surface 20 is deposited.

In various embodiments, the surface 15 of the base material 10 is treated. The surface 15 may be treated to improve binding of the synthetic polymer surface 10 to the base material surface 15, to facilitate monomer spreading on the base material surface 15, or the like. Of course, the base material 10 may be treated for similar purposes with regard to an intermediate layer 30. In various embodiments, the surface is corona treated or plasma treated. High surfaces energy obtainable from such treatments may facilitate monomer spreading and uniform coating.

It has been found that plasma treatment, compared to corona treatment of substrate formed from cyclic olefin copolymers, leads to better wettability for monomers which facilitates spreading of the monomers. In addition, it has been found that the effects on wettability of plasma treatment last longer than that of corona treatment (data not shown). For example, plasma treated surfaces can be used more than one week after treatment, while corona treated surfaces are generally ineffective unless used soon after treatment.

In embodiments of the present invention, the choice of solvent may be important. For example, some solvents such as dichloromethane (DCM) or tetrahydrofuran (THF) might dissolve commonly used substrates such as polystyrene or cyclic olefin copolymers. Or some solvents may not be appropriate for other reasons. For example N,N-dimethylformamide (DMF) has a high boiling point which would make it a poor choice for a method requiring the evaporation of a solvent at room temperature.

As described herein volatile solvents are employed, in embodiments of the present invention. When using volatile solvents, monomers that polymerize by chain polymerization are preferred relative to monomers that polymerize by step polymerization. However, step polymerization monomers may be employed in various embodiments.

In embodiments, monomers may be combined with additional monomers. In addition, monomers, either alone or mixed with additional monomers may be treated to polymerize monomers into polymers or polymeric material or polymeric blends. Many methods are known in the art for inducing polymerization, including chemical polymerization and UV polymerization. In embodiments, the monomers may be mixed with a photo-initiator composition and exposed to UV light. And, in embodiments of the present invention, to ensure uniform coating of the substrate, monomers in solution may be diluted in an appropriate organic solvent such as, for example, ethanol. In embodiments, the solvent may be, for example, ethanol. Ethanol can be removed under slight vacuum or room temperature. The choice of solvent may be very important. For example, acetone, THF (tetrahydrofuran), DCM (dichloromethane may physically interact with plastic or polymeric substrates and interfere with the long term viability of a cell culture surface. Other solvents, such as DMF (dimethylformamide), DMSO (dimethylsulfoxide), and acetonitrile are all high boiling point solvents that may require high temperature or high vacuum for evaporation and are not excluded but not preferred solvents for this process. The ethanol solvent may be, for example, a solvent having greater than about 75% ethanol. For example, an ethanol solvent may contain greater than 80%, greater than 90%, greater than 95%, greater than 97%, or greater than 99% ethanol. In various embodiments, the ethanol solvent consists essentially of ethanol. In some embodiments, an ethanol solvent consists essentially of ethanol and water. Polymerized monomers, or polymeric blends, may be applied to the substrate. In embodiments, combinations of two, three or four monomers may be polymeric blends and may be polymerized and applied to a substrate, or mixtures of two to ten or two to twenty monomers may be polymerized and applied to a surface or substrate. For example, monomers may be combined with additional monomers to provide single, bi- or trifunctional mixtures of monomers, and polymerized to form polymeric blends.

In embodiments, the synthetic polymer layer is made from at least three monomers, a hydrophilic monomer, a crosslinker monomer and a conjugator monomer which has an NHS moiety. Once the synthetic polymer layer is formed, a bioactive compound may be conjugated to the synthetic polymer layer through the NHS moiety of the conjugator monomer. Cells may be cultured on this peptide-conjugated synthetic polymer surface.

3. Culturing Cells on Peptide-Conjugated Synthetic Polymer Layer

Cells in culture, including embryonic stem cells and human embryonic stem cells, require medium. Research in the area of synthetic substrates has claimed positive results using medium supplemented with serum replacement and conditioned with mouse embryonic fibroblasts (MEFs) (Li, J. Ying, Chung, E. H., Rodriguez, Firpo, M. T., Healy, K. E., Hydrogels as Artificial matrices for Human Embryonic Stem Cell Self-Renewal, Journal of Biomedical Materials Research part A, Jun. 1, 2006, volume 79A, Issue 1, pp 1-5C). Chemically defined medium, medium in which all components are known is available from a number of vendors including, for example, Stem Cell Technologies, Invitrogen, Carlsbad Calif., and Millipore, Boston, Mass. In order to facilitate growth of a particular cell type, including undifferentiated hESC cells, as well as differentiation into particular cell types, additives such as growth factors may be added to the chemically defined media. These growth factors may include but are not limited to transforming growth factor-alpha (TGF-alpha), transforming growth factor-beta. (TGF-beta), platelet-derived growth factors including the AA, AB and BB isoforms (PDGF), fibroblast growth factors (FGF), including FGF acidic isoforms 1 and 2, FGF basic form 2, and FGF 4, 8, 9 and 10, hbFGF, nerve growth factors (NGF) including NGF 2.5 s, NGF 7.0 s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor (HGF), glial neurotrophic growth factor (GDNF), stem cell factor (SCF), keratinocyte growth factor (KGF), transforming growth factors (TGF), including TGFs alpha, beta, beta1, beta2, and beta3, skeletal growth factor, bone matrix derived growth factors, and bone derived growth factors and mixtures thereof. Some growth factors can also promote differentiation of a cell or tissue. TGF, for example, can promote growth and/or differentiation of a cell or tissue. Some preferred growth factors include VEGF, NGFs, PDGF-AA, PDGF-BB, PDGF-AB, FGFb, FGFa, hbFGF, HGF, and BGF. Medium may be conditioned, or exposed to a feeder layer of cells. In addition, serum may be added to the media. Fetal bovine serum, FBS is available from many sources including Hyclone and Sigma-Aldrich. For the purposes of the experiments described herein, X-Vivo-10 serum-free media from Lonza, Basel, Switzerland was used, amended with the addition of 80 ng/ml hbFGF and 0.5 ng/ml hTGF-β1, and included at least 20% FBS.

Stem cells include adult and embryonic stem cells. Human Embryonic cells in cell lines include CH01, CH02, CY12, CY30, CY40, CY51, CY81, CY82, CY91, CY92, CY10, GE01 (WA01, also known as H1), GE07 (WA07, H7), GE09 (WA09, H9), GE13, GE14, GE91, GE92, SA04-SA19, KA08, KA09, KA40, KA41, KA42, KA43, MB01, MB02, MB03, MI01, NC01, NC02, NC03, RL05, RL07, RL10, RL15, RL20, RL21, as well as numerous others. Stem cells may also be primary cells obtained from embryonic sources, such as surplus in vitro fertilized eggs. Examples of stem cells include, but are not limited to, embryonic stem cells, bone marrow stem cells and umbilical cord stem cells. Induced primate pluripotent stem (iPS) cells may also be used. iPS cells refer to cells, obtained from a juvenile or adult mammal, such as a human, that are genetically modified, e.g., by transfection with one or more appropriate vectors, such that they are reprogrammed to attain the phenotype of a pluripotent stem cell such as an hESC. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm and thus are suitable for differentiation into OPCs. The iPS cells, like hESC, also form teratomas when injected into immuno-deficient mice, e.g., SCID mice. (Takahashi et al., (2007) Cell 131(5):861; Yu et al., (2007) Science 318:5858). Other examples of cells used in various embodiments include, but are not limited to, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, and neurons. In one aspect, bone cells such as osteoclasts, osteocytes, and osteoblasts can be cultured with the coated substrates produced herein. Cells useful herein can be cultured in vitro, derived from a natural source, genetically engineered, or produced by any other means. Any source of cells can be used. Atypical or abnormal cells such as tumor cells can also be used herein. Cells that have been genetically engineered can also be used. Engineering involves programming the cell to express one or more genes, repressing the expression of one or more genes, or both. Genetic engineering can involve, for example, adding or removing genetic material to or from a cell, altering existing genetic material, or both. Embodiments in which cells are transfected or otherwise engineered to express a gene can use transiently or permanently transfected genes, or both. Gene sequences may be full or partial length, cloned or naturally occurring.

In the examples presented here, H1 (or WA01, or GE01) cells are used. However, it is contemplated that any cells, including stem cells or hESC may exhibit preferable characteristics when cultured on embodiments of the cell culture surfaces of the present invention.

A substrate coated with a synthetic polymer layer 20 as described above may be giving rise to a fully differentiated or mature cell types. A stem cell may be a bone marrow-derived stem cell, autologous or otherwise, a neuronal stem cell, or an embryonic stem cell. A stem cell may be nestin positive. A stem cell may be a hematopoietic stem cell. A stem cell may be a multi-lineage cell derived from epithelial and adipose tissues, umbilical cord blood, liver, brain or other organ.

Because human embryonic stem cells (hESC) have the ability to grown continually in culture in an undifferentiated state, the hESC for use in this invention may be obtained from an established cell line. Examples of human embryonic stem cell lines that have been established include, but are not limited to, H1, H7, H9, H13 or H14 (available from WiCell established by the University of Wisconsin) (Thompson (1998) Science 282:1145); hESBGN-01, hESBGN-02, hES-BGN-03 (BresaGen, Inc., Athens, Ga.); HES-1, HES-2, HES-3, HES-4, HES-5, HES-6 (from ES Cell International, Inc., Singapore); HSF-1, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., Fertil. Steril. 83(5):1517-29, 2005); lines HUES 1-17 (Cowan et al., NEJM 350(13):1353-56, 2004); and line ACT-14 (Klimanskaya et al., Lancet, 365(9471):1636-41, 2005). Embryonic stem cells used in the invention may also be obtained directly from primary embryonic tissue. Typically this is done using frozen in vitro fertilized eggs at the blastocyst stage, which would otherwise be discarded.

Other suitable stem cells include induced primate pluripotent (iPS) stem cells OPCs according to the invention may also be differentiated from induced primate pluripotent stem (iPS) cells. iPS cells refer to cells, obtained from a juvenile or adult mammal, such as a human, that are genetically modified, e.g., by transfection with one or more appropriate vectors, such that they are reprogrammed to attain the phenotype of a pluripotent stem cell such as an hESC. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm and thus are suitable for differentiation into a variety of cell types. The iPS cells, like hESC, also form teratomas when injected into immuno-deficient mice, e.g., SCID mice. (Takahashi et al., (2007) Cell 131(5):861; Yu et al., (2007) Science 318:5858).

Prior to seeding cells, the cells may be harvested and suspended in a suitable medium, such as a growth medium in which the cells are to be cultured once seeded onto the surface. For example, the cells may be suspended in and cultured in serum-containing medium, a conditioned medium, or a chemically-defined medium. As used herein, "chemically-defined medium" means cell culture media that contains no components of unknown composition. Chemically defined media may, in various embodiments, contain no proteins, hydrosylates, or peptides of unknown composition. In some embodiments, chemically-defined media contains polypeptides or proteins of known composition, such as recombinant growth hormones. Because all components of chemically-defined media have a known chemical structure, variability in culture conditions and thus cell response can be reduced, increasing reproducibility. In addition, the possibility of contamination is reduced. Further, the ability to scale up is made easier due, at least in part, to the factors discussed above. Chemically defined cell culture media are commercially available from, for example, Invitrogen (Invitrogen Corporation, 1600 Faraday Avenue, PO Box 6482, Carlsbad, Calif. 92008) as StemPro® a fully defined, serum- and feeder-free medium (SFM) specially formulated for the growth and expansion of human embryonic stem cells (hESCs), StemCell Technologies, Inc as mTeSR™1 maintenance media for human embryonic stem cells and XVivo-10, which can be supplemented with growth factors, available from Lonza.

One or more growth or other factors may be added to the medium in which cells are incubated with the synthetic polymer layer 20. The factors may facilitate cellular proliferation, adhesion, self-renewal, differentiation, or the like. Examples of factors that may be added to or included in the medium include muscle morphogenic factor (MMP), vascular endothelium growth factor (VEGF), alpha or beta transforming growth factor (TGF), interleukins, nerve growth factor (NGF), erythropoietin, platelet derived growth factor (PDGF), epidermal growth factor (EGF), activin A (ACT), such as Activin A, hematopoietic growth factors, retinoic acid (RA), interferons, fibroblastic growth factors (FGF), such as basic fibroblast growth factor (bFGF), bone morphogenetic protein (BMP), peptide growth factors, heparin binding growth factor (HBGF), hepatocyte growth factor (HGF), tumor necrosis factors (TNF), insulin-like growth factors (IGF) I and II, transforming growth factors (TGF), such as transforming growth factor-□1 (TGFβ), and colony stimulating factors.

The cells may be seeded at any suitable concentration. Typically, the cells are seeded at about 10,000 cells/cm2 of substrate to about 500,000 cells/cm2. For example, cells may be seeded at about 40,000 cells/cm2 of substrate to about 150,000 cells/cm2. However, higher and lower concentrations may readily be used. The incubation time and conditions, such as temperature, CO2 and O2 levels, growth medium, and the like, will depend on the nature of the cells being cultured and can be readily modified. The amount of time that the cells are incubated on the surface may vary depending on the cell response being studied or the cell response desired.

In general, the cell culture surfaces, synthetic polymer surfaces, were made from the combinations of conjugator monomers, hydrophilic monomers and cross-linker monomers shown in Tables 1-3 by first mixing appropriate proportions of monomers as defined below, to a solution containing a photo-initiator and a solvent. The solution was applied to a 96 well plate and distributed over the surface of the well. The solvent was allowed to evaporate. Monomers were cross-linked or polymerized using a UV light source. This method produces a polymer surface, but not an interpenetrating network. Peptides were then conjugated to the synthetic polymer surface. Cells were then cultured, in suitable media, on the surfaces. Methods for making the cell culture surfaces are described in Example 1.

Quality of cell growth, or the undifferentiated hESC attachment and proliferation on embodiments of surfaces of the present invention, was assessed by comparing the morphology of undifferentiated proliferating H1 hESC cells, including cell size, shape, and the interactions of one cell with another cell on the cell culture surfaces of the present invention with H1 hESC cells grown on Matrigel™. Matrigel™ is a basement membrane preparation extracted from mouse sarcoma cells, available from BD Biosciences, Franklin Lakes, N.J., used as a positive control for undifferentiated hES cell surface. Quality of cell growth, or the undifferentiated hESC attachment and proliferation on embodiments of (meth)acrylate surfaces of the present invention, was assessed by comparing the morphology of undifferentiated proliferating H1 hESC cells, including cell size, shape, and the interactions of one cell with another cell on the cell culture surfaces of the present invention with H1 hESC cells grown on Matrigel™ (as shown in FIG. 8A, H1 hES cells on Matrigel™ and FIGS. 8B and C, H1 hESC cells on embodiments of the (meth) acrylate surface of the present invention). Two of eight prepared NHS functionalized synthetic polymer surfaces were able to support growth and proliferation of H7 hESCs after 72 hours, i.e., HG4.1D-BSP and HG4.2C-BSP.

In embodiments, (meth)acrylate NHS ester monomers (conjugator monomers) having extended arms for longer spacing between the N-hydroxysuccinimide functionality for peptide conjugation may be used. Using conjugator monomers having extended arms may allow for controlling, i.e., increasing or decreasing peptide density, and controlling accessibility to cell binding integrins of hESCs which may bind to the conjugated peptides (such as, for example, SEQ ID NO:1 KGGNGEPRGDTYRAY, an RGD sequence from bone sialoprotein). In embodiments, this may also be accomplished by varying the concentration of the conjugator monomer in the mixture of monomers used to form synthetic polymers. In additional embodiments, crosslinker monomers of varying hydrophilicity may be used. Using hydrophilic crosslinkers, in addition to hydrophilic monomers, may increase the hydrophilicity of the synthetic polymer surface, which may provide a preferable surface for some cell types.

Figure 8:
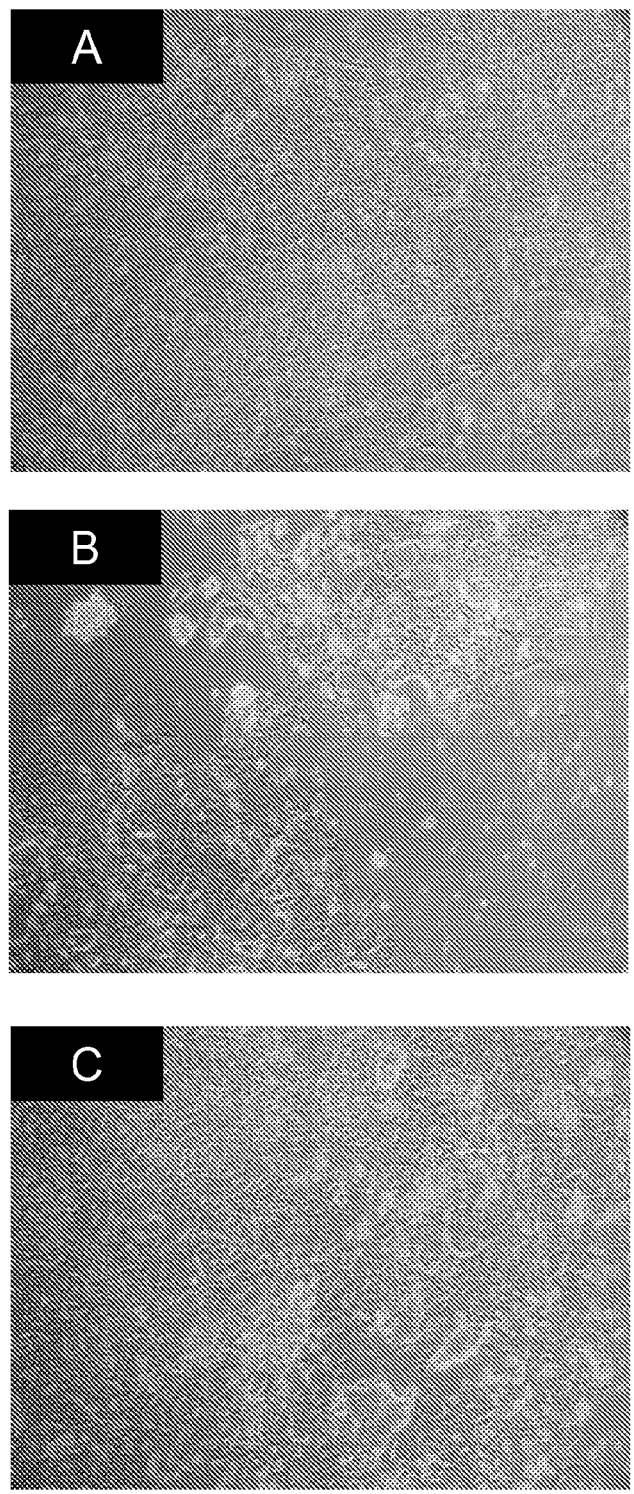
FIG. 8A-C are micrographs showing morphology of H1 human embryonic stem cells after culturing them on embodiments of the peptide-conjugated synthetic polymer surfaces of the present invention.

The integrity and uniformity of the synthetic polymer cell culture surfaces were evaluated by crystal violet blue staining, while the presence of peptide on the surfaces was measured by fluorescent spectroscopy. While all of the formulations presented in Tables 4-12 provided suitable surfaces for cell culture, two of eight prepared N-hydroxysuccinimide derived peptide-conjugated surfaces were able to facilitate growth and proliferation of H1 hESCs after 72 hrs, i.e., HG4.1D-BSP and HG4.2C-BSP, as shown in FIG. 8.

In embodiments, the cell culture surfaces of the present invention are cross-linked surfaces made from mixtures of monomer which are from about 0.1 to about 3% cross-linked, from about 0.9% to about 9% cross-linked, from about 5 to 100% cross-linker monomers, from 10-100% cross-linker monomers, from 20%-100% cross-linker monomers or from 30%-100% cross-linker monomers. Cross-linker monomers are monomers having more than one active moiety, for example (meth)acrylate moieties.

The following examples are included to demonstrate embodiments of the invention and are not intended to limit the scope of the invention in any way. It should be appreciated by those of skill in the art that the techniques disclosed in the examples which follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of Surfaces

A. Materials

Photoinitiators Irgacure 819 (Phosphine oxide, phenyl bis (2,4,6-trimethyl benzoyl) and Darocur 1173 (2-hydroxy-2-methyl-1-phenyl-1-propanone) used in the free radical polymerization of the formulations were obtained from Ciba Specialty Chemicals (Newport Delaware) and used without any further purification. Hydrophilic crosslinkers, tetraethylene glycol dimethacrylate (86680), 3-(acryloyloxy)-2-hydroxypropyl methacrylate (454982) and glycerol 1,3-diglycerol diacrylate (475807) were all purchased from Sigma-Aldrich in the purity as described in product specification sheet. Hydrophilic monomers 2-hydroxyethyl methacrylate, +99% (477028) was purchased from Sigma-Aldrich while the other hydrophilic monomer used in the formulations, glycerol monomethacrylate isomers (04180) was purchased from Polysciences Incorporated without further purification. The N-hydroxysuccinimide functionalized acrylate monomers mono-(2-methacryoyloxyl)-ethyl succinate N-hydroxysuccinimide ester and 2-carboxyethylacrylate succinate ester were synthesized according to methods disclosed in U.S. application Ser. No. 12/783,156 entitled MONOMERS FOR MAKING POLYMERIC CELL CULTURE SURFACE filed on May 19, 2010 at >95% purity. Other N-hydroxysuccinimide functionalized acrylate monomers used in formulation library, i.e., acrylic acid N-hydroxysuccinimide (A8060) was purchased from Sigma-Aldrich, in addition, acryl-poly ethylene glycol succinimide 3400 Acryl-Peg-SCM-3400 was purchased from Laysan Bio. Inc. Ethanol and isopropyl alcohol used as non-reactive diluents in the process were both purchased from Sigma-Aldrich.

B. Preparation of (Meth)Acrylates

Into a separate 20 ml scintillation vial quantities of 60 µL, 65 µL, 70 µL and 75 µL of 2-2-hydroxyethyl methacrylate was added, subsequently 40 µL, 35 µL, 30 µL, and 25 µL of the MOES-NHS or CEA-NHS ester (0.2 to 0.8 g/mL ethanol) were added along with 30 µL of 10% of tetra(ethylene glycol) dimethacrylate, 30 µL of Darocur 1173 (10% in ethanol), 10 µL Irgacure 819 (1% in ethanol) and 9.83 ml of ethanol. This recipe amounts to a 1% formulation in ethanol. Subsequently, 40 µL of IPA was added to the entire 1% formulation. All formulation libraries 4.12, 4.13, 4.2, 4.21, 4.22, 4.3, 4.31 and 4.32 are formulated using the same procedure. Formulations are shown in Tables 4-12.

C. Application of Solutions to Surfaces

Six-well plates (plasma-treated cyclic olefin copolymer (TOPAS®)) or 96 well polystyrene plates were removed from packaging and placed in large nitrogen purge box which is continuously being purged with nitrogen gas. The humidity level in the purge box was less than 30% before dispensing formulations. A semi-automated pippettor was set to 250 µL and 26 µL and dispensed into each well. The 6 well plate contained a lid with 6 "drilled holes" which allow for dispensing the formulation while at the same time controlling the evaporation rate. Once the desired amount was dispensed a solid template was placed over the drilled holes. The plate was carried to the vacuum oven and the formulation was allowed to spread for approximately 30 seconds. (Prior to this step that vacuum pump and refrigerant was turned on to ensure almost complete removal of ethanol and IPA). The solid lid was removed and replaced with a filter paper over the "drilled hole plate lid." Immediately the vacuum oven door was closed and the "vacuum" valve was adjusted to fully open. After the vacuum reached the maximum vacuum (25 to 30 in Hg.), there was a wait time of 5 minutes before closing the "vacuum" valve. The "purge" valve was released slowly until the gauge was down to "0." The instrument is designed to fill two microplates at a time. Plates were placed on trays in a hood for at least three hours until the ethanol evaporated.

D. UV Curing

A "Xenon Model RC-801 high intensity pulsed Ultraviolet (UV) light curing system", which employs the use of a single lamp that can simultaneously cure two 96 well plates at once was used in curing. The entire unit was enclosed in a chamber surrounded by a thick red curtain (UV radiation resistant). The chamber houses a purge box that holds both plates and ensures that the plates are constantly being purged with nitrogen which is necessary in order to create an inert environment (for the coatings) during curing. Once the plates have been placed in the nitrogen filled purge box and the UV chamber closed, the cure time is set (i.e. 60 sec. in this study). Also, a 60 sec purge time is also allowed prior to curing. Once the plates have been purged with nitrogen for at least 60 seconds, they are then cured by releasing a red button located on the control box of the equipment. Nitrogen purging removes oxygen from chamber and prevents scavenging or inhibition. After curing, the plates were inspected to ensure that they were properly cured; the next set of plates was cured until the desired number of plates required for curing was achieved. The plates were then set aside for quality check using crystal violet staining.

E. Peptide Conjugation

Into a 20 ml centrifuge tube, 1 mM peptide solution at pH 7.4, 25 mM PBS buffer in the amount of 1.5 mL was added to each of the 6 wells. The 6wp was placed on the shaker at a speed of 6 rpm and the peptide was allowed to react for 1.0-1.5 h. After the reaction is complete remove the peptide from the wells using an aspirator. A blocking solution of 1 M ethanolamine with pH adjusted to 8.0 to 8.5 with 37% HCl was added to each well in the amount of 1.5 mL. The 6wp were placed on the shaker for 1.0-1.5 h to allow quenching of NHS groups in the HG matrix. Directly following the blocking step the blocking solution was aspirated removing all of the blocking solution completely. Subsequently, each well was filled with 200 µL of 25 mM of phosphate buffer using a single pipettor. The buffer was then removed by aspiration after 2-5 minutes. This step was repeated 3 times, before adding DI water to the wells in the same manner, repeated 3 times. The wells were then filled with 100 µL of 1% SDS solution and the holes covered with a lid then placed on shaker between 15 minutes to overnight. Refill the wells with 300 µL of DI then aspirate completely. The plates were dried in dry ambient conditions or in vacuum oven at room temperature. The plates were individually thermo sealed in plastic pouches and stored at 2-4° C.

F. Formulations

Tables 4-12 show formulations that were prepared according to Example 1.

TABLE 4

| Formulation 4.1 | 4.1A | 4.1B | 4.1C | 4.1D |
|---|---|---|---|---|
| HEMA | 60 µL | 65 µL | 70 µL | 75 µL |
| mono-(2-methacryoyl-oxyl)-ethyl succinate N-hydroxysuccinimide ester (0.2-0.8 g/mL in EtOH) | 40 µL | 35 µL | 30 µL | 25 µL |
| TEGMDA | 30 µL | 30 µL | 30 µL | 30 µL |
| Darocur 1173 (10% in EtOH) | 30 µL | 30 µL | 30 µL | 30 µL |
| Irgacure I-819 (1% in EtOH) | 10 µL | 10 µL | 10 µL | 10 µL |
| Ethanol | 9.83 mL | 9.83 mL | 9.83 mL | 9.83 mL |

TABLE 5

| Formulation 4.12 | 4.12A | 4.12B | 4.12C | 4.12D |
|---|---|---|---|---|
| Glycerol Monomethacrylate | 60 µL | 65 µL | 70 µL | 75 µL |
| mono-(2-methacryoyl-oxyl)-ethyl succinate N-hydroxysuccinimide ester (0.2-0.8 g/mL in EtOH) | 40 µL | 35 µL | 30 µL | 25 µL |
| 3-(Acryloyloxy)-2-hydroxypropyl Methacrylate | 30 µL | 30 µL | 30 µL | 30 µL |
| Darocur 1173 (10% in EtOH) | 30 µL | 30 µL | 30 µL | 30 µL |
| Irgacure I-819 (1% in EtOH) | 10 µL | 10 µL | 10 µL | 10 µL |
| Ethanol | 9.83 mL | 9.83 mL | 9.83 mL | 9.83 mL |

TABLE 6

| Formulation 4.13 | 4.13A | 4.13B | 4.13C | 4.13D |
|---|---|---|---|---|
| Glycerol Monomethacrylate | 60 µL | 65 µL | 70 µL | 75 µL |
| mono-(2-methacryoyl-oxyl)-ethyl succinate N-hydroxysuccinimide ester (0.2-0.8 g/mL in EtOH) | 40 µL | 35 µL | 30 µL | 25 µL |
| Glycerol 1,3-Diglycerolate Methacrylate | 30 µL | 30 µL | 30 µL | 30 µL |
| Darocur 1173 (10% in EtOH) | 30 µL | 30 µL | 30 µL | 30 µL |
| Irgacure I-819 (1% in EtOH) | 10 µL | 10 µL | 10 µL | 10 µL |
| Ethanol | 9.83 mL | 9.83 mL | 9.83 mL | 9.83 mL |

TABLE 7

| Formulation 4.2 | 4.2A | 4.2B | 4.2C | 4.2D |
|---|---|---|---|---|
| HEMA | 80 µL | 80 µL | 80 µL | 80 µL |
| 2-carboxyethylacrylate N-hydroxysuccinimide ester (0.2-0.8 g/mL in EtOH) | 40 µL | 35 µL | 30 µL | 25 µL |
| CarboxyethylMethacrylate | 20 µL | 20 µL | 20 µL | 20 µL |
| TEGMDA | 30 µL | 30 µL | 30 µL | 30 µL |
| Darocur 1173 (10% in EtOH) | 30 µL | 30 µL | 30 µL | 30 µL |
| Irgacure I-819 (1% in EtOH) | 10 µL | 10 µL | 10 µL | 10 µL |
| Ethanol | 9.83 mL | 9.83 mL | 9.83 mL | 9.83 mL |
| IPA | 200 µL | 200 µL | 200 µL | 200 µL |

TABLE 8

| Formulation 4.21 | 4.2A | 4.2B | 4.2C | 4.2D |
|---|---|---|---|---|
| HEMA | 60 µL | 65 µL | 70 µL | 75 µL |
| 2-carboxyethylacrylate N-hydroxysuccinimide ester (0.2-0.8 g/mL in EtOH) | 40 µL | 35 µL | 30 µL | 25 µL |
| TEGMDA | 30 µL | 30 µL | 30 µL | 30 µL |
| Darocur 1173 (10% in EtOH) | 30 µL | 30 µL | 30 µL | 30 µL |
| Irgacure I-819 (1% in EtOH) | 10 µL | 10 µL | 10 µL | 10 µL |
| Ethanol | 9.83 mL | 9.83 mL | 9.83 mL | 9.83 mL |
| IPA | 200 µL | 200 µL | 200 µL | 200 µL |

TABLE 9

| Formulation 4.22 | 4.2A | 4.2B | 4.2C | 4.2D |
|---|---|---|---|---|
| HEMA | 80 µL | 80 µL | 80 µL | 80 µL |
| 2-carboxyethylacrylate N-hydroxysuccinimide ester (0.2-0.8 g/mL in EtOH) | 40 µL | 35 µL | 30 µL | 25 µL |

TABLE 9-continued

| Formulation 4.22 | 4.2A | 4.2B | 4.2C | 4.2D |
|---|---|---|---|---|
| CarboxyethylMethacrylate | 10 μL | 10 μL | 10 μL | 10 μL |
| TEGMDA | 30 μL | 30 μL | 30 μL | 30 μL |
| Darocur 1173 (10% in EtOH) | 30 μL | 30 μL | 30 μL | 30 μL |
| Irgacure I-819 (1% in EtOH) | 10 μL | 10 μL | 10 μL | 10 μL |
| Ethanol | 9.83 mL | 9.83 mL | 9.83 mL | 9.83 mL |
| IPA | 200 μL | 200 μL | 200 μL | 200 μL |

TABLE 10

| Formulation 4.3 | 4.3A | 4.3B | 4.3C | 4.3D |
|---|---|---|---|---|
| HEMA | 60 μL | 65 μL | 70 μL | 75 μL |
| Acryl(Polyethylene-Glycol) Succinimidyl (0.2-0.8 g/mL in EtOH) | 40 μL | 35 μL | 30 μL | 25 μL |
| TEGMDA | 30 μL | 30 μL | 30 μL | 30 μL |
| Darocur 1173 (10% in EtOH) | 30 μL | 30 μL | 30 μL | 30 μL |
| Irgacure I-819 (1% in EtOH) | 10 μL | 10 μL | 10 μL | 10 μL |
| Ethanol | 9.83 mL | 9.83 mL | 9.83 mL | 9.83 mL |

TABLE 11

| Formulation 4.31 | 4.31A | 4.31B | 4.31C | 4.31D |
|---|---|---|---|---|
| Glycerol Monomethacrylate | 60 μL | 65 μL | 70 μL | 75 μL |
| Acryl(Polyethylene-Glycol) Succinimidyl (0.2-0.8 g/mL in EtOH) | 40 μL | 35 μL | 30 μL | 25 μL |
| 3-(Acryloyloxy)-2-hydroxypropyl Methacrylate | 30 μL | 30 μL | 30 μL | 30 μL |
| Darocur 1173 (10% in EtOH) | 30 μL | 30 μL | 30 μL | 30 μL |
| Irgacure I-819 (1% in EtOH) | 10 μL | 10 μL | 10 μL | 10 μL |
| Ethanol | 9.83 mL | 9.83 mL | 9.83 mL | 9.83 mL |

TABLE 12

| Formulation 4.32 | 4.32A | 4.32B | 4.32C | 4.32D |
|---|---|---|---|---|
| Glycerol Monomethacrylate | 60 μL | 65 μL | 70 μL | 75 μL |
| Acryl(Polyethylene-Glycol) Succinimidyl (0.2-0.8 g/mL in EtOH) | 40 μL | 35 μL | 30 μL | 25 μL |
| Glycerol 1,3-Diglycerolate Methacrylate | 30 μL | 30 μL | 30 μL | 30 μL |
| Darocur 1173 (10% in EtOH) | 30 μL | 30 μL | 30 μL | 30 μL |
| Irgacure I-819 (1% in EtOH) | 10 μL | 10 μL | 10 μL | 10 μL |
| Ethanol | 9.83 mL | 9.83 mL | 9.83 mL | 9.83 mL |

All of the formulations shown in Tables 4-12 resulted in uniform cell culture surfaces, as shown by crystal violet and fluorescence studies presented below.

EXAMPLE 2

Crystal Violet Staining and Analysis of Synthetic Polymer Surfaces

Figure 5A:
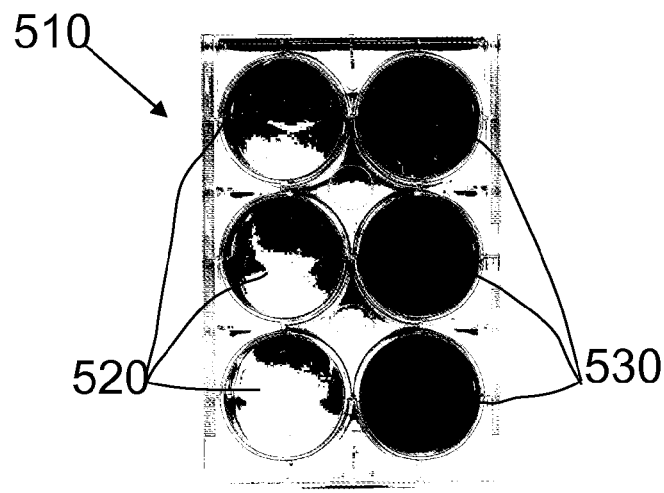
FIG. 5A is a photograph of a 6-well plate showing crystal violet stained cell culture surfaces coated according to methods of the present invention, before and after hydrolysis to remove NHS moieties.
Figure 5B:
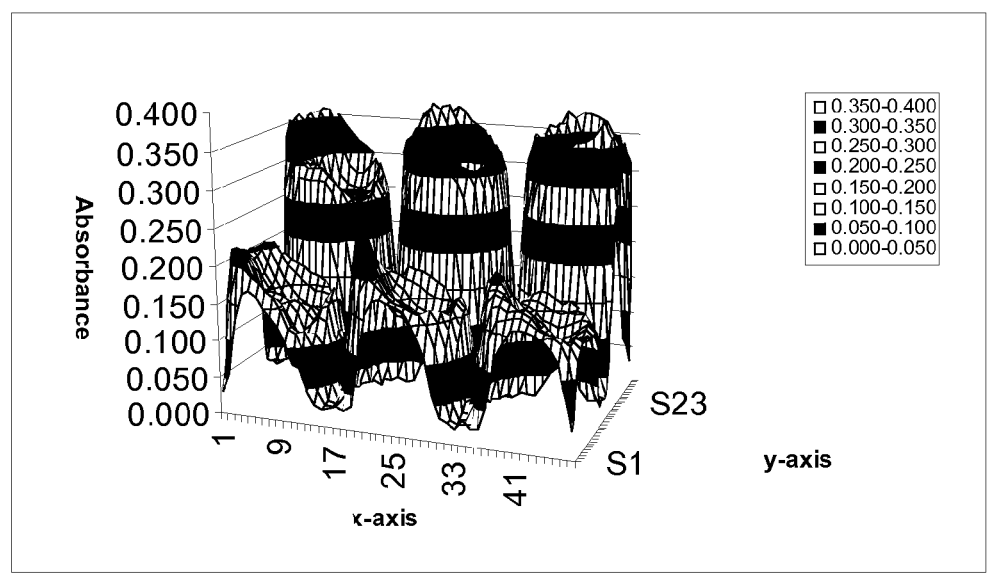
FIG. 5B is a UV/VIS plot of the same E-well plate as is shown in FIG. 5A.

As shown Formulations made according to Example 1, and described in Tables 4-12 were applied to 6-well plates. Three wells in each 6-well plate were then subjected to hydrolysis (exposure 0.1 M NaOH, pH 8) to remove N-hydroxysuccinimide moieties. FIG. 5A shows a 6-well plate 510 with three wells 520 having synthetic polymer surfaces according to Example 1 (FIGS. 5A and 5B show images and measurements from formula 4.1D from Table 4 as representative of images and measurements from all of the formulations in Tables 4-12 (data not shown)). Three wells are shown after hydrolysis to remove N-hydroxysuccinimide moieties 530 and expose COOH groups. The negative COO⁻ groups on the surface were stained with a solution of crystal violet dye in water. UV/VIS plots are shown in FIG. 5B, from the 6-well plate shown in FIG. 5A (formulation 4.1D) showing absorption levels at 570 nm achieved on staining with crystal violet, scanning the wells in the X-axis plane and the Y-axis plane.

EXAMPLE 3

Fluorescent Staining and Analysis of Cell Culture Surface

Figure 6A:
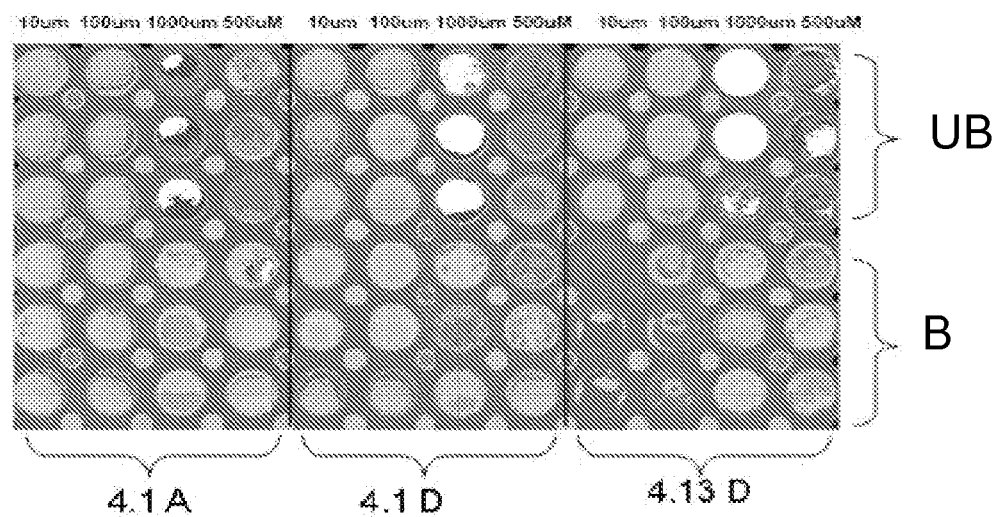
FIG. 6A is a fluorescent scan of embodiments of fluorescently labeled peptide-conjugated synthetic polymer surfaces of the present invention.

Increasing concentrations of fluorescently labeled peptide (1 μM, 10 μM, 50 μM, 100 μM, 500 μM and 1000 μM of Ac-KGGNGEPRGDTYRAY-NH$_2$ and Ac-KGGNGEPRGDTYRAY-NH$_2$—Rhodamine in at molar ratio of 99.75:0.25 (AC-SEQ ID NO:1—NH$_2$—Rhodamine) were conjugated to synthetic polymer surfaces made according to Example 1, according to the formulations shown in Tables 4-12. Representative fluorescence measurements are shown in FIG. 6A, for formulations 4.1A, 4.1D and 4.13D. FIG. 6A also shows one experimental result shows the surfaces unblocked ("UB"), and these were repeated with blocked ("B") surfaces. For the blocked surfaces, N-hydroxysuccinimide functionality was blocked ("B") prior to peptide conjugation with 3-aminopropylmorpholine.

Figure 6B:
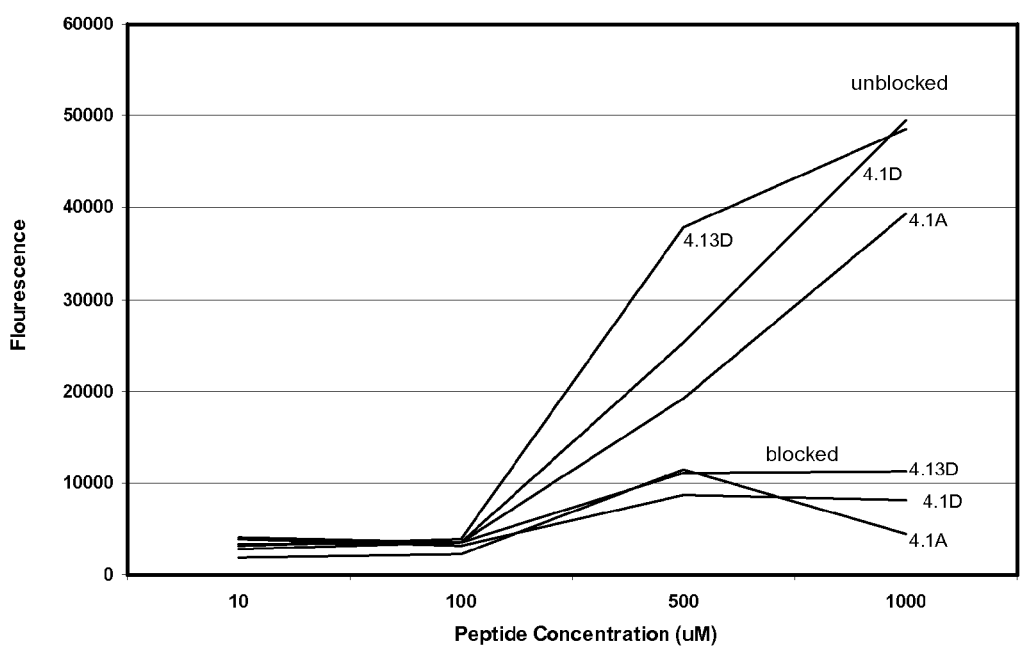
FIG. 6B is a plot of the fluorescence measured from the scan shown in FIG. 6A.
Figure 7A:
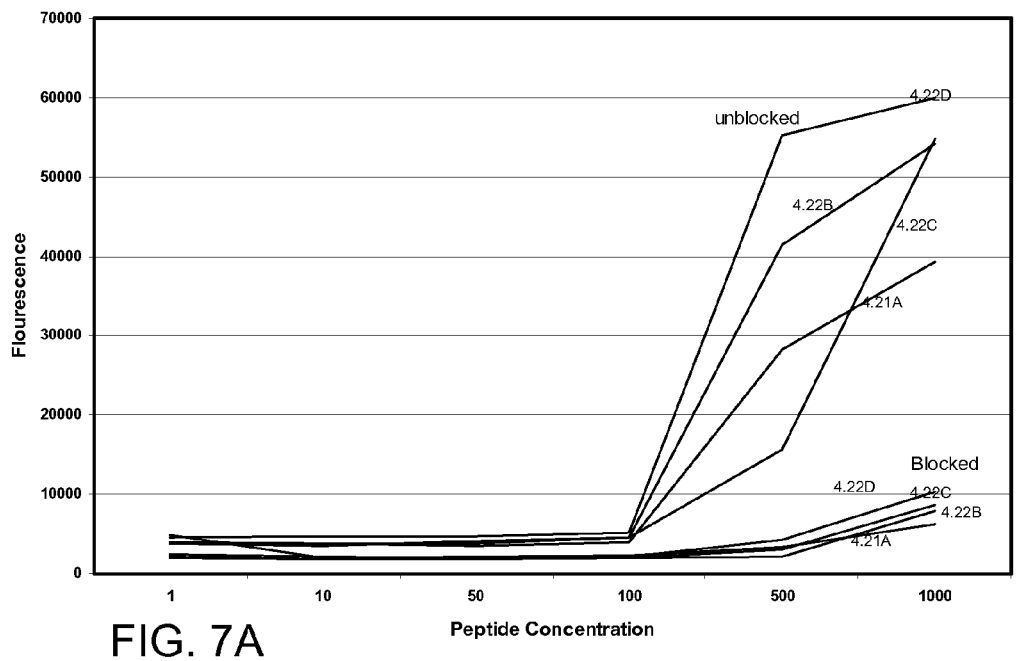
FIG. 7A and FIG. 7B are plots of fluorescence measured from fluorescence scans of embodiments of the peptide-conjugated synthetic polymer surfaces of the present invention.
Figure 7B:
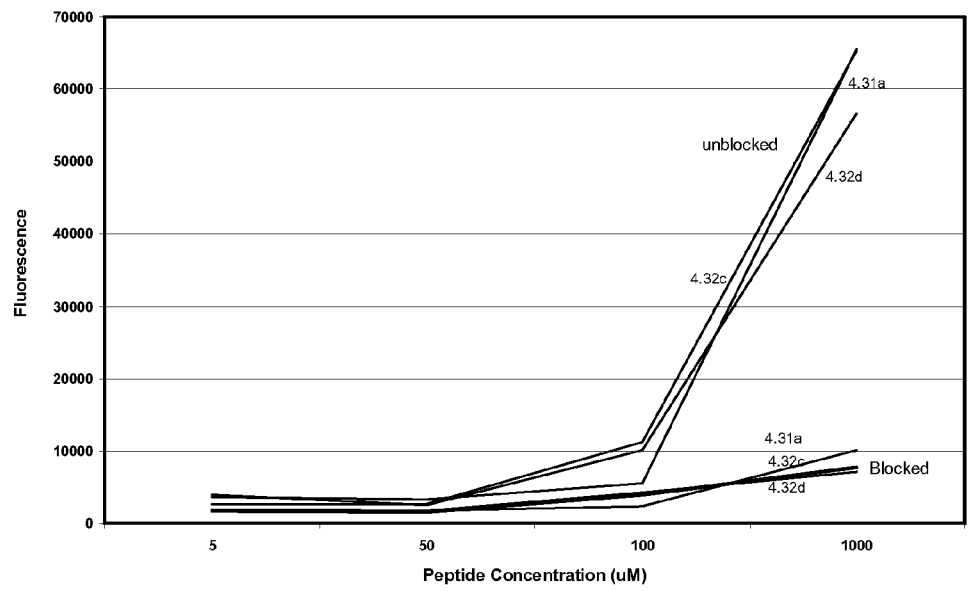

FIG. 6B is a graph showing fluorescence data (indicating peptide conjugation) for formulations 4.1A, 4.1D and 4.13D, blocked and unblocked. As can be seen in FIG. 6B, fluorescence measurements indicate that peptide conjugation can be increased by increasing the concentration of peptide exposed to the synthetic peptide surface, and peptide conjugation is blocked by 3-aminopropylmorpholine. Similarly, FIG. 7A shows fluorescence data for formulations 4.21A, 4.22B, 4.22C and 4.22D (presented in Tables 4-12), blocked and unblocked. FIG. 7B shows fluorescence data for formulations 4.31A, 4.32B, 4.32C and 4.32D (presented in Tables 4-12), blocked and unblocked.

EXAMPLE 4

Cell Culture

A. Stock Culture of hESC Cell

H1 hES cells were cultured on Matrigel-coated TCT flasks in chemically defined culture medium (X-Vivo-10, 80 ng/ml hbFGF, 0.5 ng/ml hTGF-β1). Cells were passaged every 5-6 days at the seeding density of 5×10$^6$ cells/T-75. For the experiments, cells were seeded at a density of 33,000 cells/well on Matrigel-coated or (meth)acrylate-coated 96-well plates using MultidropCombi (ThermoFisher) automated dispenser and cultured for 48 hrs in the same culture medium supplemented with 20% fetal bovine serum (FBS).

B. Culture of H1 Human Embryonic Stem Cells on Synthetic Polymer Surfaces

Prior to cell seeding, synthetic polymer surfaces prepared in the 6-well format (wells and lids) were sprayed with 70% ethanol and left to evaporate in a sterile laminar flow hood overnight. All wells were then washed twice with Dulbecco's Phosphate Buffered Saline (DPBS) to remove any residual ethanol. H1 hESCs were cultured on synthetic polymer surfaces conjugated with Ac-KGGNGEPRGDTYRAY-NH$_2$ (BSP peptide) in chemically defined cell culture medium (X-Vivo-10, 80 ng/mL hbFGF, 0.5 ng/mL hTGF-β1). Cells were seeded at the density of $0.8 \times 10^6$/well and medium was exchanged daily after 48 hours. Cells were cultured for 48 hrs under standard cell culture conditions (37° C. with 5% $CO_2$). On day 5, cells were stained with crystal violet for assessment of cell morphology. MATRIGEL™-coated wells were used as positive control for adhesion and growth of undifferentiated hES cells. Cells were cultured for 48 hrs under standard cell culture conditions (37° C. with 5% $CO_2$).

Cells were washed with 150 μl DPBS and analyzed with light microscopy (see FIG. 8 H1 hES colony morphology on synthetic polymer surfaces compared to the colony morphology on Matrigel™ (positive control). FIG. 8A is a micrograph of unstained H1 hESC cells grown on Matrigel™ (96 hours) (FIG. 8A). FIG. 8B shows unstained H1 hES cells grown on Formulation 4.1D conjugated to SEQ ID NO:1 peptide. FIG. 8C shows unstained H1 hES cells grown on formulation 4.2C conjugated to the BSP peptide. Note the similar cell morphology and colony formation.

While all of the formulations shown in Tables 4-12 resulted in peptide conjugated synthetic polymer surfaces that may be suitable for cell culture, only two of the above formulations (formulations 4.1D and 4.2C) resulted in cell culture surfaces that supported the culture of undifferentiated growth of H1 human embryonic stem cells, in the absence of serum, that was comparable to that seen for the same cells on Matrigel™. As discussed above, these cells are particularly difficult to culture, requiring conditions that allow these cells to remain in culture without differentiating.

The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

We claim:

1. A method for making a cell culture article comprising:
diluting at least three (meth)acrylate monomers in a solvent wherein at least one of the at least three (meth)acrylate monomers has an N-hydroxysuccinimide moiety;
dispersing the diluted monomers on a surface of a cell culture substrate;
removing about 80% or more of the solvent; and
polymerizing the monomers on the surface of the cell culture substrate after removing the about 80% or more of the solvent to form a synthetic polymer layer having N-hydroxysuccinimide moieties on the surface of the cell culture substrate; and,
conjugating a cell adhesive peptide to the synthetic polymer layer through the N-hydroxysuccinimide moieties.

2. The method of claim 1 wherein the at least three (meth)acrylate monomers comprise at least one hydrophilic monomer, at least one cross-linker monomer and at least one conjugator monomer.

3. The method of claim 2 wherein the conjugator monomer has an N-hydroxysuccinimide moiety.

4. The method of claim 3 wherein the conjugator comprises acrylic acid N-hydroxysuccinimide ester, 2-carboxyethylacrylate N-hydroxysuccinimide ester, mono-(2-methacryoyloxyl)-ethyl succinate N-hydroxysuccinimide ester, acryl-poly ethylene glycol succinimide 3400, or combinations of these.

5. The method of claim 3 wherein the conjugator comprises mono-(2-methacryoyloxyl)-ethyl succinate N-hydroxysuccinimide ester.

6. The method of claim 2 wherein the hydrophilic acrylate monomer comprises 2-hydroxyethyl methacrylate, glycerol monomethacrylate or combinations of these.

7. The method of claim 2 wherein the cross-linker comprises triglycerol diacrylate, 3-(acryloyloxy)-2-hydroxypropyl methacrylate or tetraethylene glycol dimethacrylate or combinations of these.

8. The method of claim 1 wherein the at least three (meth)acrylate monomers comprise 2-hydroxyethyl methacrylate, acrylic acid N-hydroxysuccinimide ester and tetraethylene glycol dimethacrylate.

9. The method of claim 1 wherein the at least three (meth)acrylate monomers comprise 2-carboxyethylacrylate N-hydroxysuccinimide ester, hydroxyethylmethacrylate and tetraethylene glycol dimethacrylate.

10. The method of claim 1 wherein the at least three (meth)acrylate monomers comprise mono-(2-methacryoyloxyl)-ethyl succinate N-hydroxysuccinimide ester, hydroxyethylmethacrylate and tetraethylene glycol dimethacrylate.

11. The method of claim 1 wherein the at least three (meth)acrylate monomers comprise acryl-poly ethylene glycol succinimide—3400, 2-hydroxyethyl methacrylate and tetraethylene glycol dimethacrylate.

12. The method of claim 1 wherein the solvent is alcohol.

13. The method of claim 12 wherein the solvent is a lower alcohol.

14. The method of claim 1 wherein the dilution step further comprises diluting a UV cross-linker in the solvent.

15. The method of claim 14 wherein the UV cross-linker is Irgacure 819 (Phosphine oxide, phenyl bis(2,4,6-trimethyl benzoyl), Darocur 1173 (2-hydroxy-2-methyl-1-phenyl-1-propanone), or a combination of these.

16. The method of claim 1 wherein the peptide comprises KGGNGEPRGDTYRAY (SEQ IDNO:1).

* * * * *